United States Patent
Niimi et al.

(10) Patent No.: US 10,751,463 B2
(45) Date of Patent: Aug. 25, 2020

(54) BLOOD CIRCULATION SYSTEM

(71) Applicant: SENKO MEDICAL INSTRUMENT Mfg. Co., Ltd., Tokyo (JP)

(72) Inventors: Yoshinari Niimi, Tokyo (JP); Katsunori Tanaka, Tokyo (JP); Masahiro Kihara, Tokyo (JP); Munehiro Kishi, Tokyo (JP); Taku Maruya, Tokyo (JP); Masanori Yoshihara, Tokyo (JP); Masahiro Kamiya, Tokyo (JP)

(73) Assignee: SENKO MEDICAL INSTRUMENT MFG. CO., LTD., Tokyo (JP)

( * ) Notice: Subject to any disclaimer, the term of this patent is extended or adjusted under 35 U.S.C. 154(b) by 490 days.

(21) Appl. No.: 15/502,091

(22) PCT Filed: Aug. 20, 2015

(86) PCT No.: PCT/JP2015/073425
§ 371 (c)(1),
(2) Date: Feb. 6, 2017

(87) PCT Pub. No.: WO2016/027866
PCT Pub. Date: Feb. 25, 2016

(65) Prior Publication Data
US 2017/0224901 A1 Aug. 10, 2017

(30) Foreign Application Priority Data

| Aug. 20, 2014 | (JP) | 2014-167559 |
| Mar. 17, 2015 | (JP) | 2015-053600 |
| Jun. 4, 2015 | (JP) | 2015-114037 |

(51) Int. Cl.
*A61M 1/36* (2006.01)
*A61M 1/10* (2006.01)
*A61M 1/16* (2006.01)

(52) U.S. Cl.
CPC ........ *A61M 1/3666* (2013.01); *A61M 1/1029* (2014.02); *A61M 1/1037* (2013.01);
(Continued)

(58) Field of Classification Search
CPC .............. A61M 1/3666; A61M 1/1029; A61M 1/1039; A61M 1/1603; A61M 1/1629;
(Continued)

(56) References Cited

U.S. PATENT DOCUMENTS

| 4,598,697 A | 7/1986 | Numazawa |
| 4,650,457 A | 3/1987 | Morloka |

(Continued)

FOREIGN PATENT DOCUMENTS

| CN | 102365105 A | 2/2012 |
| DE | 19622184 A1 | 12/1997 |

(Continued)

OTHER PUBLICATIONS

Office Action for JP Patent Application No. 2015-114878, dated Jan. 8, 2019, in 6 pages.

(Continued)

*Primary Examiner* — Ariana Zimbouski
(74) *Attorney, Agent, or Firm* — Procopio, Cory, Hargreaves & Savitch LLP

(57) ABSTRACT

An artificial heart and lung apparatus includes a roller pump; a blood removal line; a first blood transfer line; a blood removal rate sensor; a control unit that performs the linked control of the roller pump in correspondence with a blood removal rate; and a blood transfer rate adjustment unit that instructs the roller pump to transfer a blood transfer rate. The blood transfer rate adjustment unit includes an operation amount input unit to which an operation amount from an arbitrary circumferential position can be input, and which outputs a pulse signal according to the input operation (Continued)

amount. A counter adds and subtracts pulse signals output from the operation amount input unit, and outputs a resultant as blood transfer rate adjustment data. The counter performs a counting operation with respect to the circumferential position of the operation amount input unit when blood transfer control transitions to the normal control.

2 Claims, 12 Drawing Sheets

(52) U.S. Cl.
CPC ........ *A61M 1/1039* (2014.02); *A61M 1/1046* (2013.01); *A61M 1/1086* (2013.01); *A61M 1/1603* (2014.02); *A61M 1/1629* (2014.02); *A61M 1/1698* (2013.01); *A61M 1/3624* (2013.01); *A61M 1/3639* (2013.01); *A61M 1/101* (2013.01); *A61M 1/1006* (2014.02); *A61M 2205/18* (2013.01); *A61M 2205/3303* (2013.01); *A61M 2205/3306* (2013.01); *A61M 2205/3334* (2013.01); *A61M 2205/3365* (2013.01); *A61M 2205/3375* (2013.01); *A61M 2205/50* (2013.01); *A61M 2205/502* (2013.01)

(58) Field of Classification Search
CPC .............. A61M 1/1037; A61M 1/1046; A61M 1/1086; A61M 1/1698; A61M 1/3624; A61M 1/3639
See application file for complete search history.

(56) References Cited

U.S. PATENT DOCUMENTS

| | | | |
|---|---|---|---|
| 5,813,972 | A | 9/1998 | Nazarlan |
| 6,024,692 | A | 2/2000 | Dilling |
| 2010/0042259 | A1 | 2/2010 | Simons |
| 2010/0106101 | A1* | 4/2010 | Fisher ................. A61M 39/288 604/250 |
| 2012/0273415 | A1 | 11/2012 | Gerber |
| 2012/0330214 | A1 | 12/2012 | Peters et al. |
| 2015/0045712 | A1 | 2/2015 | Ninomiya et al. |

FOREIGN PATENT DOCUMENTS

| | | |
|---|---|---|
| EP | 2519282 B1 | 11/2012 |
| EP | 2711037 A1 | 3/2014 |
| GB | 2538577 | 11/2016 |
| JP | 62-027966 A | 2/1987 |
| JP | 63-143078 A | 6/1988 |
| JP | 2000-000299 A | 1/2000 |
| JP | 2000210381 A | 8/2000 |
| JP | 2000245829 A | 9/2000 |
| JP | 2001-517495 A | 10/2001 |
| JP | 2006-020712 A | 1/2006 |
| JP | 2006043045 A | 2/2006 |
| JP | 2006-325750 A | 12/2006 |
| JP | 2010-517734 A | 5/2010 |
| JP | 2011147710 A | 8/2011 |
| JP | 2013501578 A | 1/2013 |
| JP | 2014046026 A | 3/2014 |
| WO | 80/02376 A1 | 11/1980 |
| WO | 92/02264 A1 | 2/1992 |
| WO | 99/15212 A1 | 4/1999 |
| WO | 2011019655 A2 | 2/2011 |
| WO | 2011/079941 A1 | 7/2011 |
| WO | 2012/141756 A2 | 10/2012 |
| WO | 2013/012776 A1 | 1/2013 |
| WO | 2013/025826 A1 | 2/2013 |
| WO | 2013/128016 A1 | 9/2013 |
| WO | 2013128012 A1 | 9/2013 |
| WO | 2014/121164 A1 | 8/2014 |
| WO | 2015/041150 A1 | 3/2015 |

OTHER PUBLICATIONS

International Search Report and Written Opinion for PCT App No. PCT/JP2015/073425 dated Nov. 2, 2015, 9 pgs.
International Search Report and Written Opinion for PCT App No. PCT/JP2015/073428 dated Nov. 2, 2015, 8 pgs.
International Search Report and Written Opinion for PCT App No. PCT/JP2015/073363 dated Nov. 2, 2015, 9 pgs.
Communication Pursuant to Article 94(3) EPC for EP App No. 15833783.2 dated Apr. 20, 2018, 5 pgs.
Extended European Search Report for related EP Patent Application No. 15832993.8, dated Jun. 23, 2017, in 7 pages.
Extended European Search Report for related EP Patent Application No. 15833783.2, dated Jun. 29, 2017, in 8 pages.
Office Action for related U.S. Appl. No. 15/502,949, dated Jun. 29, 2017, in 6 pages.
Chinese Office Action dated Dec. 18, 2017 for Chinese Patent Application No. 201580042928.9, 12 pages.
Notice of Reasons for Rejection for related JP App No. 2015-157773 dated Jul. 23, 2019, 6 pgs.
Office Action for related U.S. Appl. No. 15/502,949 dated Sep. 19, 2019, 7 pages.
Notice of Reasons for Rejection for related JP App No. 2015-146146 dated Feb. 5, 2019, 6 pgs.

* cited by examiner

BLOOD CIRCULATION SYSTEM

TECHNICAL FIELD

The present invention relates to a blood circulation system that circulates removed blood via a blood transfer pump.

CROSS-REFERENCE TO RELATED APPLICATIONS

This application is a U.S. National Stage entry of PCT Application No. PCT/JP2015/073425, filed on Aug. 20, 2015, which priority is claimed on Japanese Patent Application No. 2014-167559, filed Aug. 20, 2014, Japanese Patent Application No. 2015-053600, filed Mar. 17, 2015, and Japanese Patent Application No. 2015-114037, filed Jun. 4, 2015, the contents of which are incorporated herein by reference.

BACKGROUND ART

In the related art, an artificial heart and lung and a blood circulation system for adjunctively circulating blood are widely used as necessary when a heart is stopped or is approximately stopped during or after surgery such as cardiac surgery.

As shown in FIG. 12, an artificial heart and lung apparatus (blood circulation system) 500 equipped with an artificial heart and lung in the related art includes a blood removal line 501; a reservoir 502; a blood line 603; a blood transfer line 504; a first blood transfer line 505; an artificial lung 506; and a second blood transfer line 507.

The blood removal line 501 transfers blood, which has been received from a vein of a patient (human body) P, to the reservoir 502. The blood removal line 501 is a tube formed of resin such as polyvinyl chloride.

The reservoir 502 includes a tank therein, and temporarily stores the transferred blood.

The blood transfer pump 504 transfers the blood stored in the reservoir 502 to the artificial lung 506 via the blood line 503 through which the reservoir 502 is connected to the blood transfer pump 504, and via the first blood transfer line 505 through which the blood transfer pump 504 is connected to the artificial lung 506. For example, a roller pump or a centrifugal pump is used as the blood transfer pump 504. The blood transfer pump 504 is controlled by a signal output from a blood transfer pump control unit 540.

The artificial lung 506 includes a hollow fiber membrane, a flat membrane, or the like having good gas permeability, and has the function of discharging carbon dioxide from and adding oxygen to blood.

The second blood transfer line 507 receives the blood, from which carbon dioxide has been discharged and to which oxygen has been added by the artificial lung 506, and transfers the blood to an artery of the patient P.

Advanced knowledge and techniques are required to operate the artificial heart and lung apparatus 500 with such a configuration. Typically, a clinical engineer adjusts a blood flow rate via a manual operation according to a doctor's instructions.

When adjusting the blood flow rate via a manual operation, the clinical engineer is required to adjust a blood flow rate in the blood removal line 501 by pinching the blood removal line 501 with a forceps while confirming the degree of removal of blood or an arterial pressure of the patient.

Since the clinical engineer adjusts the amount of discharge of the blood transfer pump by manually controlling the rotational speed of the blood transfer pump (roller pump, centrifugal pump, or the like) when adjusting the blood flow rate, a complex and advanced operation technique is required in addition to the adjustment of each line.

Patent Document 1 discloses technology to adjust a blood removal rate in which the blood removal line 501 is pinched and deformed to accurately and simply adjust the blood removal rate via an artificial heart and lung apparatus.

In order to adjust the flow rate of blood to be removed via the blood removal line 501, the artificial heart and lung apparatus disclosed in Patent Document 1 pinches and deforms the blood removal line 501 by operating a blood removal regulator 521, which includes a clamper formed of a pair of clamp members and a servo motor, via a blood removal regulator operation unit 520.

Patent Document 2 discloses technology in which a blood removal regulator control unit is linked with a blood transfer regulator control unit, a blood removal rate and a blood transfer rate are simultaneously controlled via operation of one of the control units, and thus a blood flow rate of an artificial heart and lung apparatus is efficiently adjusted.

CITATION LIST

Patent Document

[Patent Document 1] Japanese Unexamined Patent Application, First Publication No. 62-027966
[Patent Document 2] Japanese Unexamined Patent Application, First Publication No. 2006-020712

SUMMARY OF INVENTION

Technical Problem

The amount of blood to be removed may change defending on surgical situations, and a blood circulate system which is capable of stably transferring blood even if a blood removal rate changes significantly is required.

The blood circulation system capable of stably transferring blood is desirably capable of efficiently circulating blood.

The present invention is made in light of this problem, and an object of the present invention is to provide a blood circulation system that is capable of stably transferring blood and efficiently circulating blood.

Solution to Problem

In order to solve this problem, the present invention proposes the following means.

According to a first aspect of the present invention, a blood circulation system that can be connected to a human body, and transfers removed blood to the human body via a blood transfer pump, includes: the blood transfer pump; a blood removal line through which removed blood flows to the blood transfer pump; a blood transfer line that transfers blood, which is sent from the blood transfer pump, to the human body; blood removal rate measurement means that is provided in the blood removal line; a control unit that performs the linked control of the blood transfer pump in correspondence with a blood removal rate measured by the blood removal rate measurement means such that a blood transfer rate of the blood transfer pump is in a specific range with respect to the blood removal rate; and blood transfer rate instruction means for instructing a target blood transfer rate of the blood transfer pump in normal control in which the blood transfer pump transfers blood independently from the blood removal rate. The blood transfer rate instruction means includes a blood transfer rate adjustment unit. The blood transfer rate adjustment unit includes an operation amount input unit to which an operation amount from an arbitrary position can be input, and which outputs a pulse signal according to the input operation amount and a counter that adds and subtracts pulse signals output from the operation amount input unit, and outputs a resultant as blood transfer rate adjustment data, and the counter performs a counting operation with respect to the position of the operation amount input unit when blood transfer control transitions to the normal control.

In the blood circulation system of the invention, the control unit performs the linked control of the blood transfer pump in correspondence with the blood removal rate such that the blood transfer rate is in a specific range with respect to the blood removal rate. Therefore, even if the blood removal rate changes, it is possible to stably circulate blood.

In a case where the blood transfer control transitions from the linked control to the normal control, regardless of a previous operation amount before transitioning to the linked control, the position of the blood transfer rate adjustment unit when transitioning to the normal control is used as a reference. Accordingly, in a case where an operation amount such as a volume is mechanically set, typically, it is difficult to automatically reset a reference position. For this reason, in the blood circulation system, in a case where the linked control is not continuously performed, and the blood transfer control transitions to the normal control, the volume or the like is desirably manually reset (for example, reset to a reference position such as zero). In contrast, in the blood transfer rate adjustment unit of the invention, it is possible to eliminate the labor and time required to manually reset a volume or the like.

Since it is possible to adjust the blood transfer rate from an arbitrary position of the blood transfer rate adjustment unit, in a case where the linked control is not continuously performed, and the blood transfer control transitions to the normal control, it is possible to adjust the blood transfer rate with respect to a position after the blood transfer control transitions to the normal control. For this reason, it is not necessary to manually reset the volume or the like, and thus, the blood circulation system is capable of efficiently adjusting a blood transfer flow in the normal control without stopping.

In a case where the blood transfer rate in the linked control is significantly smaller than a blood transfer rate that is set by the blood transfer rate adjustment unit in the normal control before the blood transfer control transitions to the linked control, it is possible to prevent blood from being transferred at the previous blood transfer rate, which has been set by the blood transfer rate adjustment unit, after the blood transfer control transition to the normal control, and it is possible to stably circulate blood.

In the present invention, the blood removal line represents a blood line among blood lines of the blood circulation system which is formed such that blood removed from the human body flows through the blood line toward the blood transfer pump. More specifically, the blood removal line represents a blood line leading toward a reservoir. The blood transfer line represents a blood line leading toward the human body from the blood transfer pump.

In a blood circulation path, a blood line, which is positioned on the downstream side of a portion (for example, reservoir) in which blood opens to a space and in which there is no normal continuity of a blood flow rate, may not represent the blood removal line or the blood transfer line.

For the sake of convenience, a blood line may indicate a portion of the blood removal line and the blood transfer line.

In the present invention, the linked control implies that the transferring of blood performed by the blood transfer pump is controlled while being linked with the blood removal rate. The linked control implies that the blood transfer rate of the blood transfer pump is controlled to be in a specific range with respect to the blood removal rate.

In the present invention, the fact that the blood transfer rate is in a specific range with respect to the blood removal rate implies that the blood transfer rate is in a range of conditions which is set in advance with respect to the blood removal rate. The specific range can be represented by a difference in flow rate (for example, an upper limit or lower limit difference in flow rate) with respect to the blood removal rate.

In the present invention, the synchronization of the blood transfer rate with the blood removal rate implies that the blood transfer rate of the blood transfer pump is set to be equal to the blood removal rate, and includes a case in which the blood transfer rate exactly coincides with blood removal rate, and a case in which the blood transfer rate substantially coincides with the blood removal rate. That is, errors caused by a time lag of a control signal output to the blood transfer pump or a response time of the blood transfer pump are allowed.

The synchronization includes a case in which the same amount of blood as the amount of removed blood is transferred by the blood transfer pump when the transferring of blood is delayed by an amount of time set in advance.

In the present invention, the normal control implies that the blood transfer rate of the blood transfer pump is controlled independently from the blood removal rate, and implies that the blood transfer rate is controlled while not being linked with the blood removal rate. The normal control includes a case in which control is performed according to an instruction regarding a blood transfer rate which is given by a manual operation, and a case in which control is performed according to data (including data stored in the storage means) set in advance.

In the present invention, needless to say, the blood removal rate measurement means includes measurement means for measuring a blood removal rate, and includes measurement means for measuring various blood removal rate parameters for specifying a blood removal rate.

The blood removal rate parameters are parameters which change in correspondence with a blood removal rate, and include a blood removal rate. The blood removal rate parameters include various parameters for specifying a blood removal rate, for example, the flow speed of removed blood in a case where a cross-sectional flow path area of the blood removal line is already known, and a parameter (for example, a change in ultrasonic wave frequency) for specifying the flow speed.

The fact that the blood transfer rate of the blood transfer pump is set to be in a specific range of blood removal rates measured by the blood removal rate measurement means includes a case in which the blood removal rate is not calculated, and according to measured values of the blood removal rate parameters, the blood transfer pump is directly controlled in order for the blood transfer rate to be in a specific range.

In the present invention, an operation amount input unit, to which an operation amount from an arbitrary position can be input, and which outputs a pulse signal according to an input operation amount, is considered to have the following configuration. An encoder, in which an instruction output and a circumferential position (rotational position) are not in a fixed one-to-one relationship and which is capable of having an arbitrary position as a reference (zero) for use in inputting an operation amount, regardless of the position (including a rotational angle, a circumferential position, or the like) of a knob or the like, corresponds to the operation amount input unit. The blood transfer rate adjustment unit may not include an encoder.

The position of the input unit implies the circumferential position (rotational angle) of a rotary knob. In a case where the input unit includes a pair of (+) press switch and (−) press switch, and increases or decreases an operation amount according to the number of presses thereof, the position of the input unit implies the number of presses of a press switch.

According to a second aspect of the present invention, in the first aspect, the blood transfer rate instruction means includes a linked blood transfer rate storage unit that stores data relating to a linked blood transfer rate when the blood transfer control transitions from the linked control to the normal control. In addition, in a case where the blood transfer control transitions from the linked control to the normal control, the control unit controls the blood transfer rate according to the data relating to a linked blood transfer rate which is stored in the linked blood transfer rate storage unit.

In the blood circulation system of the invention, the blood transfer rate instruction means includes the linked blood transfer rate storage unit, and the linked blood transfer rate storage unit is capable of storing the data relating to a linked blood transfer rate when the blood transfer control transitions from the linked control to the normal control. Accordingly, in a case where the blood transfer control transitions from the linked control to the normal control, the blood transfer rate instruction means is capable of controlling the blood transfer rate according to the data relating to a linked blood transfer rate which is stored in the linked blood transfer rate storage unit.

As a result, even if the blood removal rate changes during the linked control, and deviates from a blood transfer rate set before the linked control, it is possible to efficiently perform adjustment with reference to the blood transfer rate when the blood transfer control transitions from the linked control to the normal control.

According to a third aspect of the present invention, in the first or second aspect, the blood transfer rate adjustment unit includes an encoder with a knob through which an operation amount from an arbitrary position can be input.

Since the blood transfer rate adjustment unit includes the encoder with the knob through which an operation amount from an arbitrary position (circumferential position) can be input, the blood circulation system of the invention has a simple structure, and is capable of efficiently adjusting the blood transfer rate.

In a case where the blood transfer control transitions from the linked control to the normal control, the blood transfer rate in the normal control is adjusted without manually setting the knob to a specific reference position. As a result, it is possible to eliminate the labor and time required to return the knob to a specific reference position, and it is possible to efficiently provide an instruction of a blood transfer rate after the blood transfer control transitions from the linked control to the normal control.

Advantageous Effects of Invention

The blood circulation system of the invention is capable of stably transferring blood and efficiently circulating blood.

Since it is possible to adjust the blood transfer rate from an arbitrary circumferential position of the encoder, in a case where the linked control is not continuously performed, and the blood transfer control transitions to the normal control, it is possible to adjust the blood transfer rate with respect to a circumferential position after the blood transfer control transitions to the normal control. Accordingly, the blood circulation system is capable of efficiently adjusting the blood transfer rate in the normal control without stopping.

In a case where the blood transfer rate in the linked control is significantly smaller than a blood transfer rate that is set by the blood transfer rate adjustment unit in the normal control before the blood transfer control transitions to the linked control, it is possible to prevent blood from being transferred at the previously set blood transfer rate, after the blood transfer control transitions to the normal control and it is possible to stably circulate blood.

DESCRIPTION OF EMBODIMENTS

First Embodiment

Hereinafter, an artificial heart and lung apparatus (blood circulation system) of a first embodiment of the present invention will be described with reference to FIGS. 1 to 6.

Figure 1:
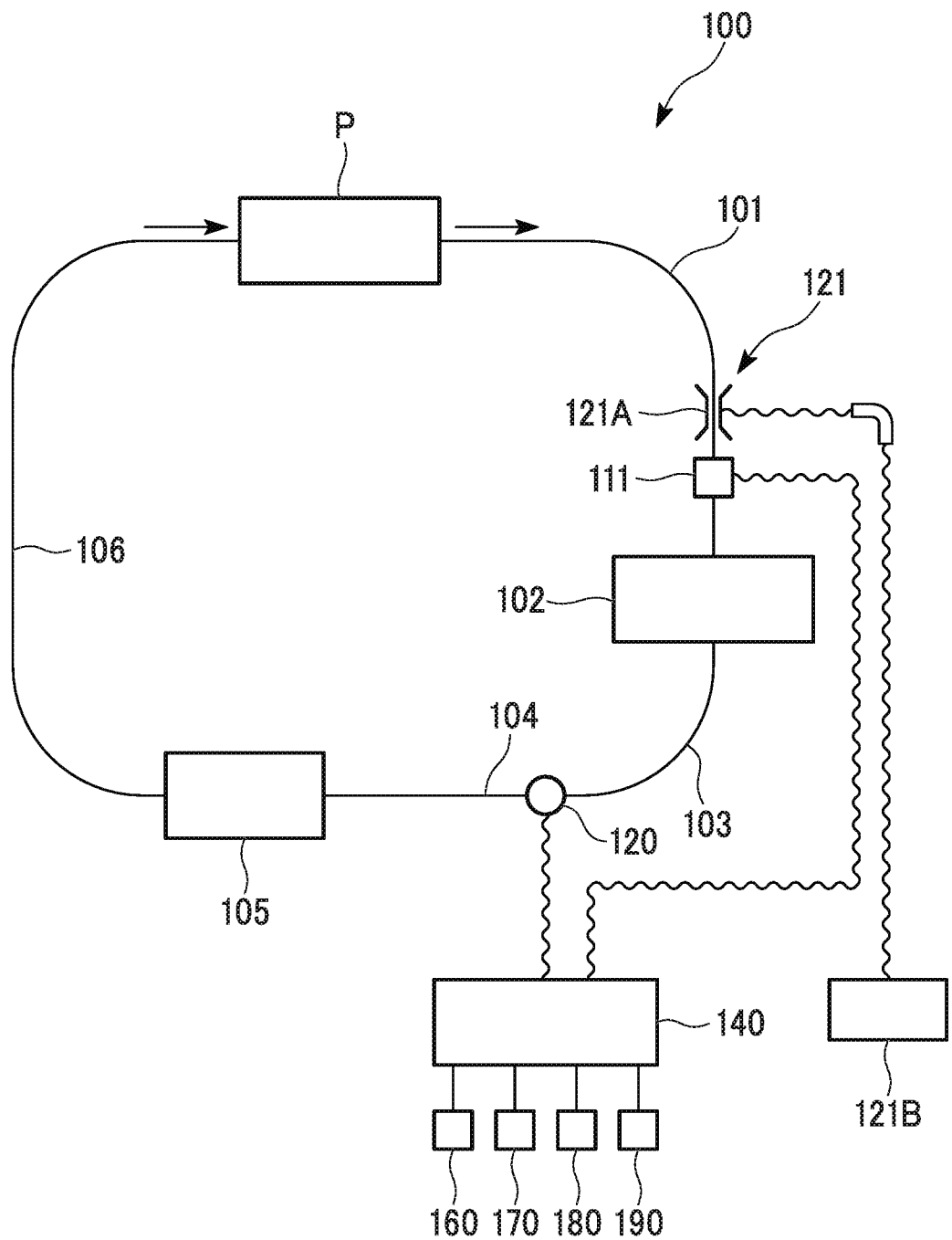
FIG. 1 is a circuit diagram showing a schematic configuration of an artificial heart and lung apparatus of a first embodiment of the present invention.

FIG. 1 is a circuit diagram showing a schematic configuration of the artificial heart and lung apparatus of the first embodiment of the present invention. Reference sign 100 represents an artificial heart and lung apparatus, a reference sign 111 represents a blood removal rate sensor, reference sign 120 represents a roller pump, a reference sign 140 represents a control unit, a reference sign 160 represents a blood transfer rate adjustment unit (blood transfer rate instruction means), and a reference sign 170 represents a linked blood transfer rate storage unit.

As shown in FIG. 1, the artificial heart and lung apparatus 100 includes a blood removal line 101; a reservoir 102; a blood line 103; a first blood transfer line (blood transfer line) 104; an artificial lung 105; a second blood transfer line (blood transfer line) 106; a blood removal rate sensor (blood removal rate measurement means) 111; a roller pump (blood transfer pump) 120; a blood removal regulator (flow rate adjustment means) 121; a control unit 140; a blood transfer rate adjustment unit 160; a linked blood transfer rate storage unit 170; a linked control display unit 180; and a blood transfer control switching unit 190.

In the embodiment, the blood transfer rate instruction means is formed of the blood transfer rate adjustment unit 160 and the linked blood transfer rate storage unit 170.

The blood removal line 101, the reservoir 102, the blood line 103, the roller pump 120, the first blood transfer line 104, the artificial lung 105, and the second blood transfer line 106 are connected together in the listed sequence. The blood removal regulator 121 and the blood removal rate sensor 111 are disposed in the blood removal line 101 in the listed sequence.

Blood to be removed via the blood removal line 101 is circulated to a patient (human body) P via the first blood transfer line 104 and the second blood transfer line 106.

The blood removal line 101 is a tube formed of resin such as polyvinyl chloride. One end of the blood removal line 101 can be connected to the patient P, and transfers blood, which has been received from a vein, to the reservoir 102.

A sensor or the like (not shown) is provided in the blood removal line 101 so as to monitor the concentration of blood or the concentration of oxygen as necessary. The sensor or the like may be provided in the blood line 103 or the first blood transfer line 104 instead of the blood removal line 101.

The reservoir 102 includes a tank therein, and temporarily stores the transferred blood.

A suction line (not shown) is connected to the reservoir 102 so as to suction blood in a surgical site of the patient P, and a vent line (not shown) is connected to the reservoir 102 so as to suction blood in a right cardiac chamber.

The blood line 103 has the same configuration as that of the blood removal line 101. The upstream side of the blood line 103 is connected to the reservoir 102, and the downstream side of the blood line 103 is connected to the roller pump 120. The blood line 103 transfers the blood, which has been received from the reservoir 102, to the roller pump 120.

The roller pump 120 includes a rotating roller and a tube that is disposed on the outside of the rotating roller and is formed of flexible resin. If the rotating roller rotates and wipes the tube, and blood is suctioned and transferred out, the blood stored in the reservoir 102 is suctioned via the blood line 103, and is transferred to the artificial lung 105 via the first blood transfer line 104.

The rotational speed of the rotating roller is controlled by a rotation control signal output from the control unit 140, and the roller pump 120 suctions and transfers an amount of blood in correspondence with the rotational speed of the rotating roller.

The first blood transfer line 104 has the same configuration as that of the blood removal line 101. The upstream side of the first blood transfer line 104 is connected to the roller pump 120, and the downstream side of the first blood transfer line 104 is connected to the artificial lung 105. The first blood transfer line 104 transfers the blood, which has been transferred out from the roller pump 120, to the artificial lung 105.

The artificial lung 105 includes a hollow fiber membrane, a flat membrane, or the like having good gas permeability, and discharges carbon dioxide from and adds oxygen to blood.

A heat exchanger is formed integrally with the artificial lung 105 so as to adjust the temperature of blood.

The second blood transfer line 106 has the same configuration as that of the blood removal line 101, and receives the blood, from which carbon dioxide has been discharged and to which oxygen has been added, from the artificial lung 105, and transfers the blood to an artery of the patient P.

A filter (not shown) is provided in the second blood transfer line 106 so as to remove foreign matter such as thrombi and bubbles from blood.

The blood removal regulator 121 is provided in the blood removal line 101. The blood removal regulator 121 includes a clamper 121A formed of a pair of clamp members; a servo motor (not shown) that operates the clamper 121A; and a blood removal regulator operation unit 121B. An operator changes the cross-sectional area of the blood removal line 101 by adjusting the amount of clamp (the amount of pinch) of the clamper 121A via the servo motor driven by manually operating the blood removal regulator operation unit 121B, and as a result, the removal rate of blood flowing through the blood removal line 101 is adjusted.

The blood removal rate sensor (blood removal rate measurement means) 111 is provided in the blood removal line 101. An ultrasonic sensor which measures the flow speed of blood via ultrasonic waves is used as the blood removal rate sensor 111. The blood removal rate sensor 111 transmits a measured blood removal rate signal (blood removal rate parameter signal) to the control unit 140.

Figure 2:
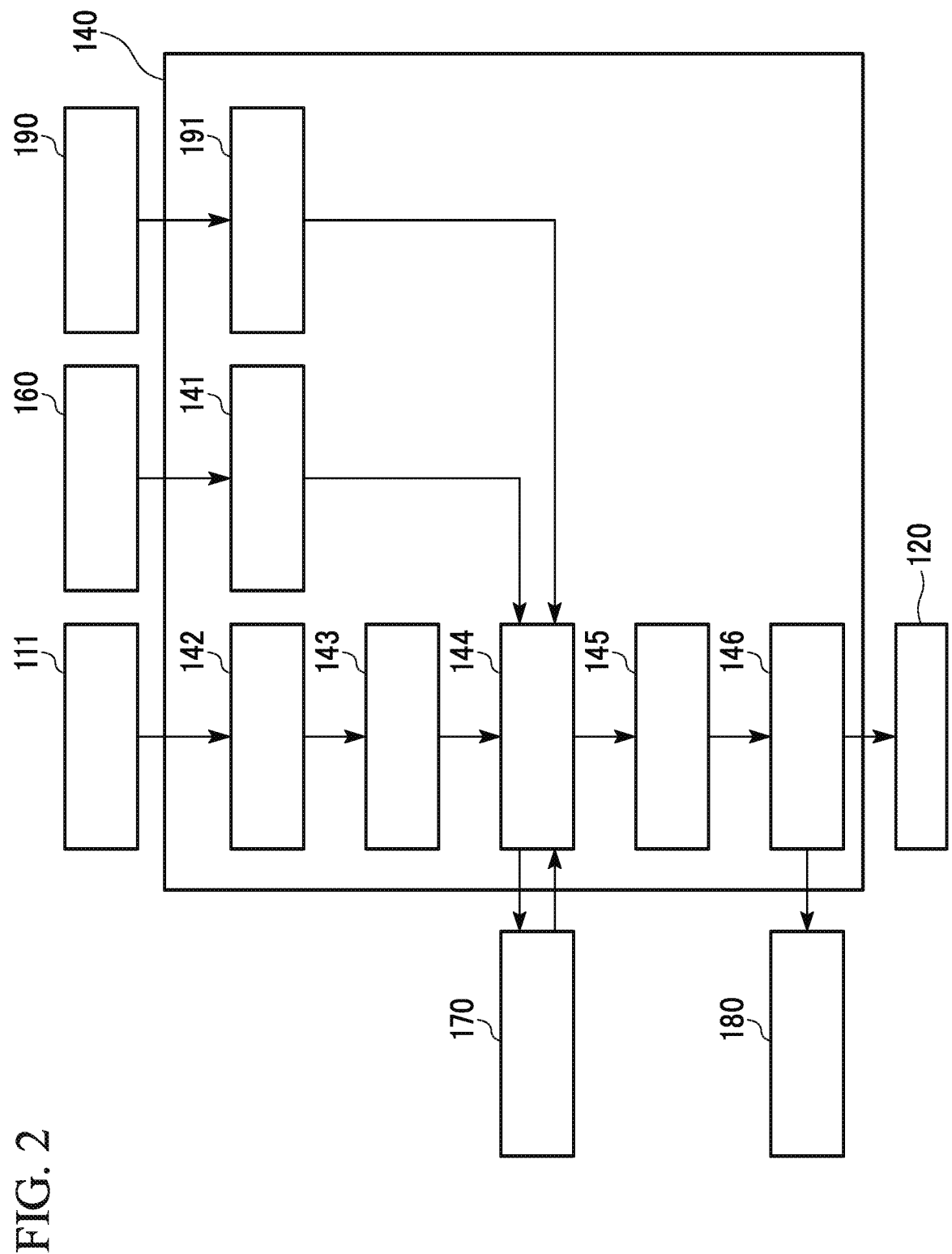
FIG. 2 is a block diagram showing a schematic configuration of a control unit of the artificial heart and lung apparatus of the first embodiment of the present invention.

Hereinafter, a schematic configuration of the control unit 140 will be described with reference to FIG. 2. FIG. 2 is a block diagram showing the schematic configuration of the control unit 140 of the first embodiment.

The control unit 140 includes a blood transfer rate adjustment data receiving unit 141; a blood removal rate signal input reserving unit 142; a blood removal rate calculation unit 143; a blood transfer rate calculation unit 144; a roller pump control amount calculation unit 145; a roller pump control unit 146; and a blood transfer control switching instruction receiving unit 191.

The control unit 140 is connected to the blood removal rate sensor 111, the blood transfer rate adjustment unit 160, the linked blood transfer rate storage unit 170, the linked control display unit 180, the blood transfer control switching unit 190, and the roller pump 120 via cables.

The blood transfer rate adjustment unit 160 is configured to input a blood transfer rate (target blood transfer rate, and hereinafter, may be simply referred to as a blood transfer rate in the first embodiment) to the roller pump 120 in the artificial heart and lung apparatus 100. For example, the blood transfer rate adjustment unit 160 includes an encoder (operation amount input unit) and a counter.

If a latch positioned at an arbitrary circumferential position is rotated with respect to the arbitrary circumferential position, an increase and decrease in operation amount can be input to the encoder, and the encoder outputs pulse signals according to an input operation amount.

The counter adds and subtracts the pulse signals output from the encoder, and outputs a resultant as blood transfer rate adjustment data. If blood transfer control transitions from normal control to linked control, and the normal control stops, an operation amount obtained via addition and subtraction up to that point is reset.

In a case where blood transfer control transitions from the linked control to the normal control, or in a case where the artificial heart and lung apparatus 100 stops and the normal control starts afresh, the blood transfer rate adjustment unit 160 is capable of adjusting the blood transfer rate by inputting a new increase and decrease in operation amount with respect to the circumferential position regardless of the circumferential position of the knob of the encoder.

The linked blood transfer rate storage unit 170 is formed of an external memory or the like. In the embodiment, the linked blood transfer rate storage unit 170 stores a blood transfer rate (data relating to a linked blood transfer rate) in the linked control which is calculated by the blood transfer rate calculation unit 144.

The linked control display unit 180 is formed of a LED lamp. In a case where the linked control of the roller pump 120 is performed, the linked control display unit 180 is turned on by an output of the roller pump control unit 146 to display a control state (normal control or linked control) of the roller pump 120, and thus, an operator is notified of the control state.

The blood transfer control switching unit 190 is configured to instruct the artificial heart and lung apparatus 100 to transfer blood in either the normal control or the linked control. The blood transfer control switching unit 190 includes an alternative switch.

The blood transfer control switching unit 190 may include multiple configuration elements such as a sensor which detect abnormality occurring the artificial heart and lung apparatus 100 and instructs the artificial heart and lung apparatus 100 to transition to the normal control.

The blood transfer rate adjustment data receiving unit 141 is connected to the blood transfer rate adjustment unit 160, and receives blood transfer rate adjustment data (the amount of increase and decrease in blood transfer rate) sent from the blood transfer rate adjustment unit 160.

The blood removal rate signal input receiving unit 142 is connected to the blood removal rate sensor 111, and receives a blood removal rate signal (blood removal rate parameter signal) sent from the blood removal rate sensor 111.

The blood removal rate calculation unit 143 calculates a blood removal rate according to the blood removal rate signal sent from the blood removal rate signal input receiving unit 142. Specifically, the blood removal rate calculation unit 143 calculates a blood removal rate by multiplying a blood removal speed (flow rate parameter), which is calculated from the blood removal rate signal, by a flow path area of the blood removal line 101.

The blood transfer rate calculation unit 144 calculates blood transfer rates (target blood transfer rates) of the roller pump 120 in the normal control and the linked control.

The calculation of a blood transfer rate performed by the blood transfer rate calculation unit 144 switches between the normal control and the linked control according to linked control transition conditions sot in advance or a blood transfer control switching instruction signal received from the blood transfer control switching instruction receiving unit 191.

The blood transfer rate calculation unit 144 calculates a blood transfer rate in the normal control according to the blood transfer rate adjustment data received from the blood transfer rate adjustment data receiving unit 141 and the blood transfer rate read from the blood transfer rate storage unit 170.

In the linked control the blood transfer rate calculation unit 144 stores the calculated blood transfer rate (target blood transfer rate) in the linked blood transfer rate storage unit 170.

In the embodiment, in the linked control, a blood transfer rate (target blood transfer rate) of the roller pump 120 is set to coincide with a blood removal rate, and the blood transfer rate is synchronized with the blood removal rate.

The synchronization of the blood transfer rate of the roller pump 120 with the blood removal rate is one aspect in which the blood transfer rate is controlled to be in a specific range (for example, in a range represented by a ratio to the blood removal rate, or in a range represented by a difference in flow rate with respect to the blood removal rate) with respect to the blood removal rate.

The blood transfer rate calculation unit 144 performs a blood transfer rate (target blood transfer rate) calculation process in the normal control as described below.

<Blood Transfer Rate Calculation Process in Normal Control>

Figure 3:
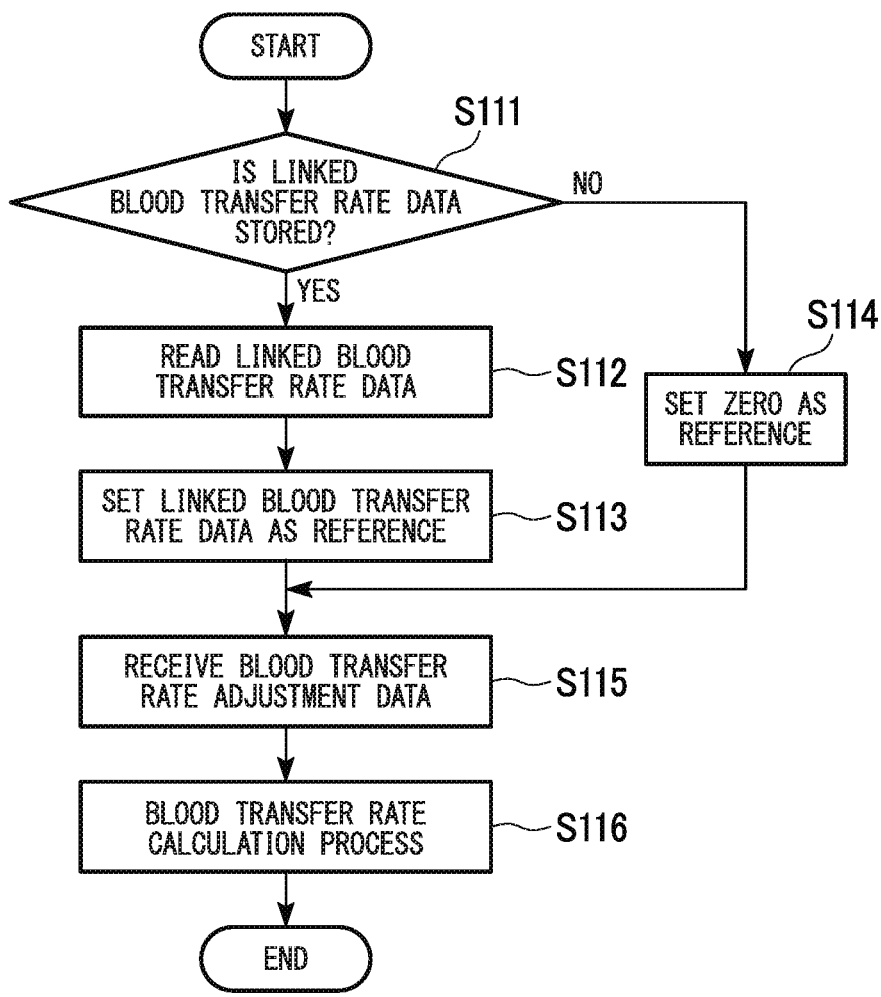
FIG. 3 is a flowchart showing an example of a blood transfer rate calculation process in the normal control of the artificial heart and lung apparatus of the first embodiment of the present invention.

Hereinafter, an example of the blood transfer rate calculation process of calculating a blood transfer rate in the normal control of the artificial heart and lung apparatus 100 of the first embodiment will be described with reference to FIG. 3. FIG. 3 is a flowchart showing an example of the blood transfer rate calculation process in the normal control which is performed by the blood transfer rate calculation unit 144.

(1) First, the blood transfer rate calculation unit 144 determines whether the linked blood transfer rate storage unit 170 stores linked blood transfer rate data (S111).

In a case where the linked blood transfer rate data is stored (S111: Yes), the process proceeds to S112. In a case where there is no instruction indicating a transition to the linked control (S111: No), the process proceeds to S114.

(2) Subsequently, the blood transfer rate calculation unit 144 reads the linked blood transfer rate data from the linked blood transfer rate storage unit 170 (S112).

(3) The blood transfer rate calculation unit 144 sets the read linked blood transfer rate data as a reference when calculating a blood transfer rate (S113). If S113 is executed, the process proceeds to S115.

(4) The blood transfer rate calculation unit 144 sets "zero" as a reference when calculating a blood transfer rate (S114).

(5) Subsequently, the blood transfer rate calculation unit 144 receives blood transfer rate adjustment data (S115).

(6) Subsequently, the blood transfer rate calculation unit 144 calculates a blood transfer rate (target blood transfer rate) according to the received blood transfer rate adjustment data (S116).

In the calculation of the blood transfer rate, for example, the blood transfer rate adjustment data is added to (increased or decreased) the reference set in S113 or S114.

While the normal control of the artificial heart and lung apparatus 100 is performed, the process from S111 to S116 is repeatedly executed at predetermined intervals.

The roller pump control amount calculation unit 145 calculates a rotational speed (control amount) to be output to the roller pump 120 in each of the normal control and the linked control according to the blood transfer rate sent from the blood transfer rate calculation unit 144.

The rotational speed of the roller pump 120 is calculated by referring to a data table representing a relationship between the rotational speed and the blood transfer rate of the roller pump 120 which represents a blood transfer rate characteristic of the roller pump 120, or by computing a calculation expression representing the relationship between the rotational speed and the blood transfer rate of the roller pump 120.

The rotational speed of the roller pump 120 which is set for the linked control is a rotational speed for synchronizing a blood transfer rate of the roller pump 120 with a blood removal rate.

The roller pump control unit 146 outputs a signal to the roller pump 120 in correspondence with the control amount received from the roller pump control amount calculation unit 145.

In a case where blood transfer control transitions to the linked control, the roller pump control unit 146 turns on the linked control display unit 180.

<Normal Control>

Figure 4:
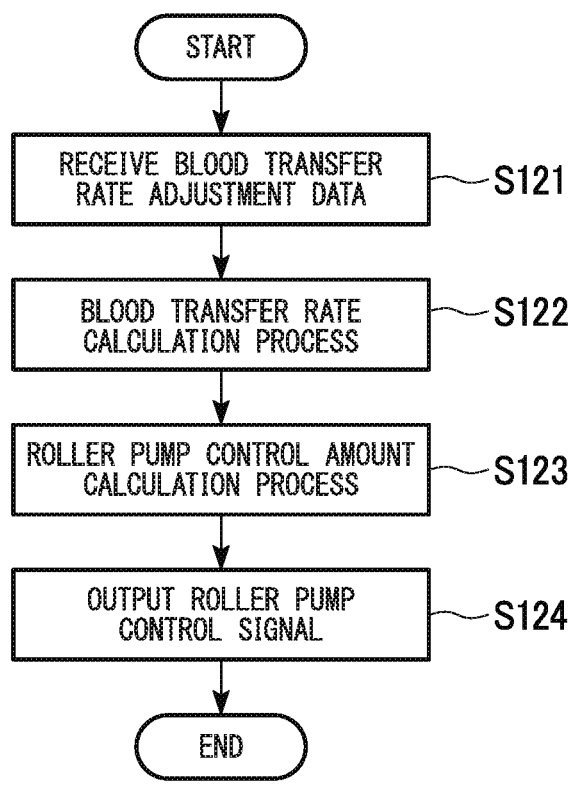
FIG. 4 is a flowchart showing an example of an operational sequence in the normal control of the artificial heart and lung apparatus of the first embodiment of the present invention.

Hereinafter, an example of an operational sequence in a case where the normal control of a blood transfer rate is performed by operating the blood transfer rate adjustment unit 160 of the artificial heart and lung apparatus 100 will be described with reference to FIG. 4. FIG. 4 is a flowchart showing an example of the operational sequence in the normal control of the artificial heart and lung apparatus 100.

The operational sequence in the normal control of the artificial heart and lung apparatus 100 is as described below.

(1) First, the blood transfer rate adjustment data receiving unit 141 receives blood transfer rate adjustment data (S121).

(2) Subsequently, the blood transfer rate calculation unit 144 calculates a blood transfer rate according to the received blood transfer rate adjustment data (S122).

(3) Subsequently, the roller pump control amount calculation unit 145 calculates a control amount (rotational speed) according to the blood transfer rate characteristic of the roller pump 120 according to the blood transfer rate calculated in S122 (S123).

(4) Subsequently, the roller pump control unit 146 outputs a signal to the roller pump 120 in correspondence with the control amount (S124).

Until the artificial heart and lung apparatus 100 transitions to the linked control, the process from S121 to S124 is repeatedly executed at predetermined intervals.

<Linked Control>

Figure 5:
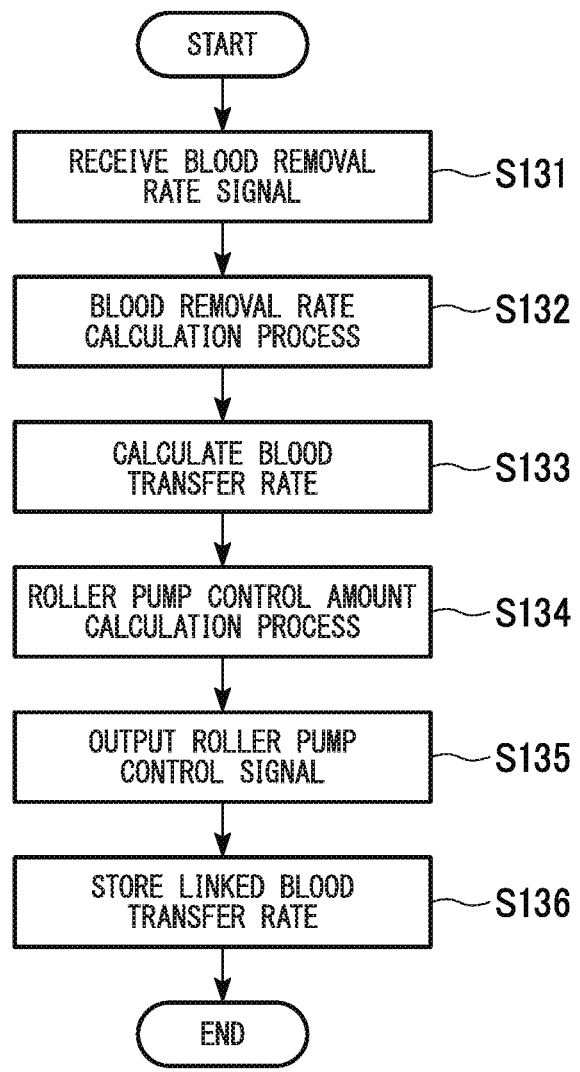
FIG. 5 is a flowchart showing an example of an operational sequence in the linked control of the artificial heart and lung apparatus of the first embodiment of the present invention.

Hereinafter, an example of an operational sequence in the linked control of the artificial heart and lung apparatus 100 will be described with reference to FIG. 5. FIG. 5 is a flowchart showing an example of the operational sequence in the linked control of the artificial heart and lung apparatus 100.

(1) First, the blood removal rate signal input receiving unit 142 receives a blood removal rate signal (blood removal rate parameter signal) (S131).

(2) Subsequently, the blood removal rate calculation unit 143 calculates a blood removal rate according to the received blood removal rate signal (S132).

(3) Subsequently, the blood transfer rate calculation unit 144 calculates a blood transfer rate according to the calculated blood removal rate (S133).

In a case where the blood transfer rate is synchronized with the blood removal rate, the blood transfer rate calculated according to the blood removal rate is equal to the blood removal rate. The blood transfer rate may be set such that an absolute value of (the blood transfer rate minus the blood removal rate) is in a predetermined range.

(4) Subsequently, the roller pump control amount calculation unit 145 calculates a control amount (rotational speed) of the roller pump 120 according to the calculated blood transfer rate (S134).

The control amount (rotational speed) of the roller pump 120 according to a blood transfer rate is calculated according to the blood transfer rate characteristic of the roller pump 120.

(5) Subsequently, the roller pump control unit 146 outputs a signal to the roller pump 120 in correspondence with the control amount (S135).

(6) Subsequently, the blood transfer rate calculation unit 144 stores the blood transfer rate (data relating to a linked blood transfer rate), which has been calculated in S133, in the linked blood transfer rate storage unit 170 (S136).

The process from S131 to S136 is repeatedly executed at predetermined intervals until blood transfer control transitions to the normal control or surgery is complete and the linked control ends.

<Switching between Normal Control and Linked Control>

Figure 6:
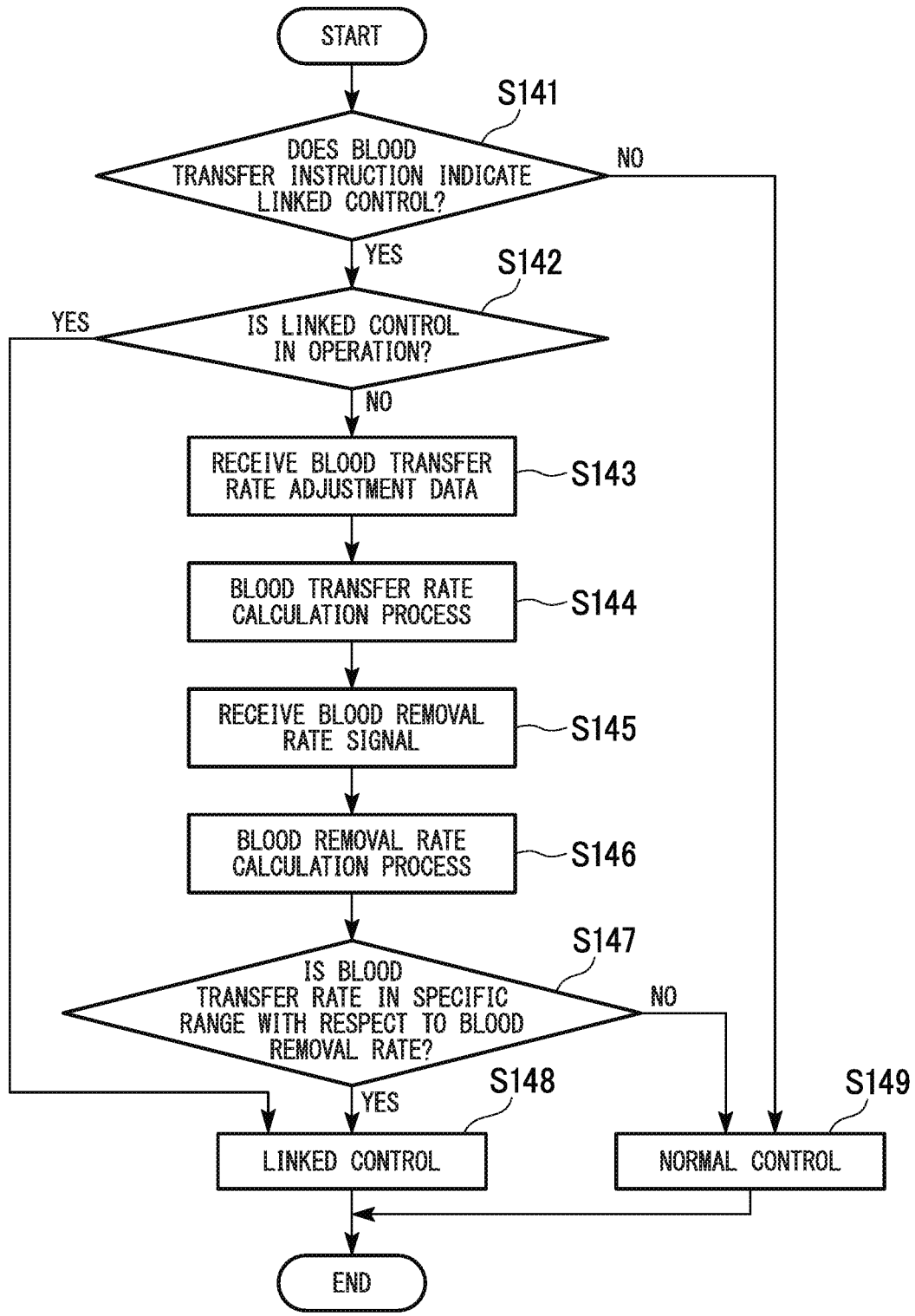
FIG. 6 is a flowchart showing switching of the artificial heart and lung apparatus of the first embodiment of the present invention between the normal control and the linked control.

Hereinafter, an example of switching of the artificial heart and lung apparatus 100 of the first embodiment between the normal control and the linked control will be described with reference to FIG. 6. FIG. 6 is a flowchart showing an example of the switching of the artificial heart and lung apparatus 100 between the normal control and the linked control.

The switching of the artificial heart and lung apparatus 100 between the normal control and the linked control is performed in the following sequence.

(1) First, the blood transfer control switching unit 190 determines whether a blood transfer switching instruction indicates the linked control (S141).

In a case where the blood transfer switching instruction indicates the linked control (S141: Yes), the process proceeds to S142. In a case where the blood transfer switching instruction does not indicate the linked control (indicates the normal control) (S141: No), the process proceeds to S149.

(2) Subsequently, the blood transfer control switching instruction receiving unit 191 determines whether the linked control is in operation (S142).

In a case where the linked control is not in operation (S142: No), the process proceeds to S143. In a case where the linked control is in operation (S142: Yes), the process proceeds to S148.

A determination as to whether the linked control is in operation is made according to whether a flag indicating that the blood transfer control switching unit 190 switches blood transfer control to the linked control is set, and whether the flag is erased when the process proceeds to S148 thereafter.

(3) Subsequently, the blood transfer rate adjustment data receiving unit 141 receives blood transfer rate adjustment data (S143).

(4) Subsequently, the blood transfer rate calculation unit 144 calculates a blood transfer rate according to the received blood transfer rate adjustment data (S144).

(5) Subsequently, the blood removal rate signal input receiving unit 142 receives a blood removal rate signal (blood removal rate parameter signal) (S145).

(6) Subsequently, the blood removal rate calculation unit 143 calculates a blood removal rate according to the received blood removal rate signal (S146).

(7) Subsequently, it is determined whether the calculated blood transfer rate is in a specific range with respect to the calculated blood removal rate (S147).

Specifically, it is determined whether an absolute value of ((the blood transfer rate) minus (the blood removal rate)) is in a specific range (blood flow rate).

In a case where whether the absolute value of (the blood transfer rate) minus (the blood removal rate) is less than or equal to K (the specific range) (S147: Yes), the artificial heart and lung apparatus 100 transitions to the linked control (S148). In a case where whether the absolute value of (the blood transfer rate) minus (the calculated blood removal rate) is greater than K (the specific range) (S147; No), the artificial heart and lung apparatus 100 transitions to the normal control (S149).

The process from S141 to S149 is repeatedly executed at predetermined intervals while the artificial heart and lung apparatus 100 is in operation.

In the artificial heart and lung apparatus 100 of the first embodiment, the control unit 140 synchronizes the blood transfer rate of the roller pump 120 with the blood removal rate. As a result, even if the blood removal rate changes, it is possible to stably circulate blood.

Since the blood transfer rate adjustment unit 160 includes an encoder with a knob through which an operation amount from an arbitrary position (circumferential position) can be input, the artificial heart and lung apparatus 100 of the first embodiment has a simple structure. That is, in a case where blood transfer control transitions from the linked control to the normal control, it is not necessary to reset the blood transfer rate adjustment unit 160 by manually returning the blood transfer rate adjustment unit 160 to a specific reference position. As a result, adjustment of the normal control can be efficient due to the elimination of the labor and time required to perform a reset.

In the artificial heart and lung apparatus 100 of the first embodiment, in a case where the blood transfer rate of the roller pump 120 in the linked control is significantly smaller than a blood transfer rate that is set by the blood transfer rate adjustment unit in the normal control before the blood transfer control transitions to the linked control, it is possible to prevent blood from being transferred at the previous blood transfer rate, which has been set by the blood transfer rate adjustment unit, after transitioning to the normal control, and it is possible to stably circulate blood.

In a case where the linked control is not continuously performed, and blood transfer control transitions to the normal control, it is possible to adjust the normal control without the stopping of the blood circulation system, and thus, it is possible to efficiently circulate blood.

In the artificial heart and lung apparatus 100 of the first embodiment, the blood transfer rate (data relating to a linked blood transfer rate) of the roller pump 120 when blood transfer control transitions from the linked control to the normal control is stored in the linked blood transfer rate storage unit 170, and it is possible to adjust a blood transfer rate in the normal control with respect to the blood transfer rate stored in the linked blood transfer rate storage unit 170. Accordingly, even if a blood removal rate which is set before the blood transfer control transitions to the linked control significantly changes after transitioning to the linked control, it is possible to stably adjust a blood transfer rate after transitioning to the normal control.

Since the artificial heart and lung apparatus 100 of the first embodiment includes the roller pump 120 as the blood transfer pump, the artificial heart and lung apparatus 100 is prevented from being affected by pressure, and it is possible to transfer blood at a stable blood transfer rate.

In the artificial heart and lung apparatus 100 of the first embodiment, the blood removal regulator 121 is provided in the blood removal line 101, and thus, it is possible to suitably adjust the flow rate of blood to be removed via the blood removal line 101.

Second Embodiment

Hereinafter, an artificial heart and lung apparatus (blood circulation system) of a second embodiment of the present invention will be described with reference to FIGS. 7 to 11.

Figure 7:
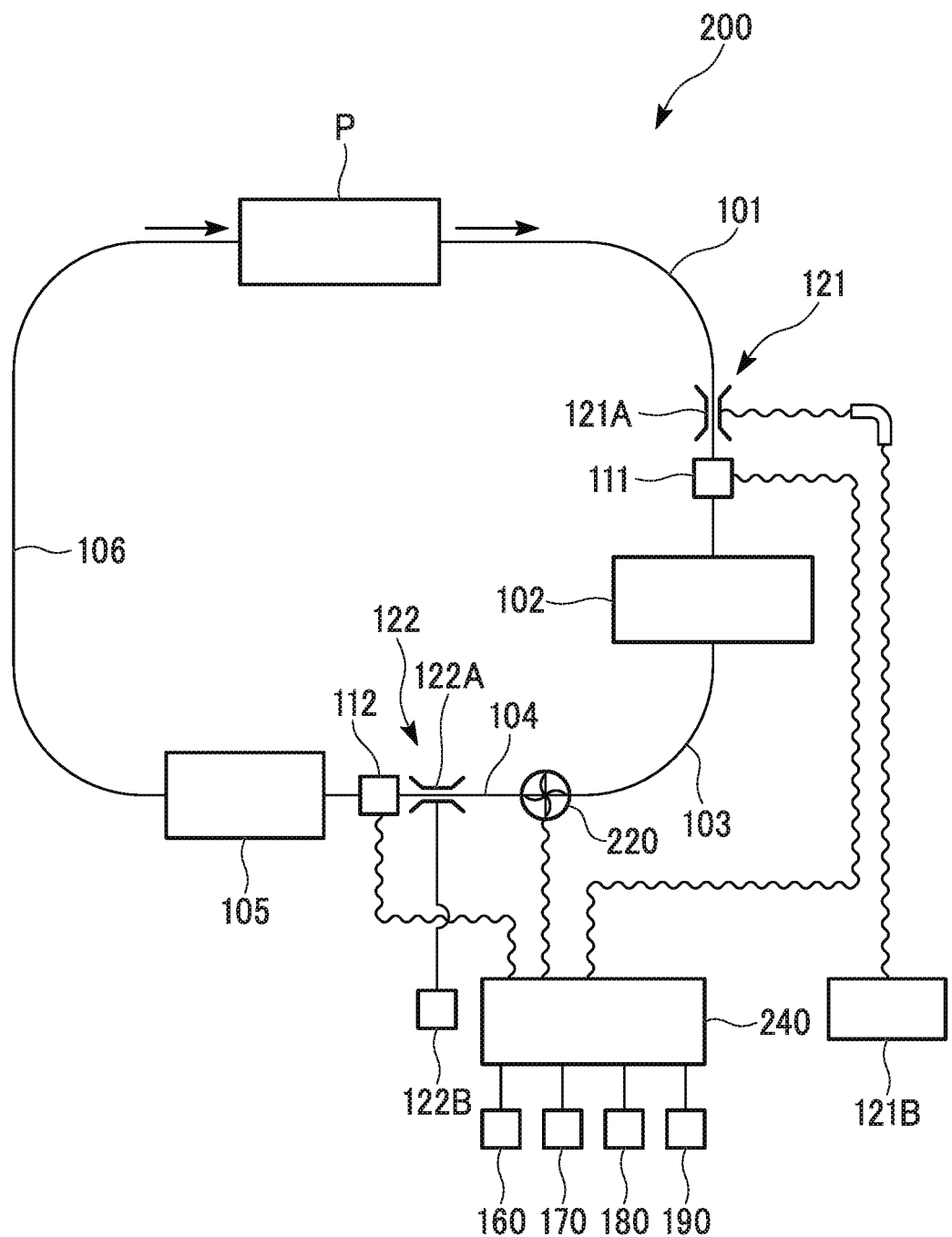
FIG. 7 is a circuit diagram showing a schematic configuration of an artificial heart and lung apparatus of a second embodiment of the present invention.

FIG. 7 is a circuit diagram showing a schematic configuration of the artificial heart and lung apparatus of the second embodiment. Reference sign 200 represents an artificial heart and lung apparatus, reference sign 112 represents a blood transfer rate sensor (blood transfer rate measurement means), reference sign 220 represents a centrifugal pump (blood transfer pump), and reference sign 240 represents a control unit.

As shown in FIG. 7, an artificial heart and lung apparatus 200 includes the blood removal line 101; the reservoir 102; the blood line 103; a centrifugal pump 220; the first blood transfer line (blood transfer line) 104; the artificial lung 105; the second blood transfer line (blood transfer line) 106; the blood removal rate sensor 111; a blood transfer rate sensor 112; the blood removal regulator (flow rate adjustment means) 121; a blood transfer regulator 122; a control unit 240; the blood transfer rate adjustment unit (blood transfer rate instruction means) 160; the linked blood transfer rate storage unit 170; the linked control display unit 180; and the blood transfer control switching unit 190.

The blood removal line 101 the reservoir 102, the blood line 103, the centrifugal pump 220, the first blood transfer line 104, the artificial lung 105, and the second blood transfer line 106 are connected together in the listed sequence. The blood removal regulator 121 and the blood removal rate sensor 111 are disposed in the blood removal line 101 in the listed sequence. The blood transfer regulator 122 and the blood transfer rate sensor 112 are disposed in the first blood transfer line 104 in the listed sequence.

The blood removal line 101, the reservoir 102, the blood line 103, the first blood transfer line 104, the artificial lung 105, the second blood transfer line 106, the blood removal rate sensor 111, the blood removal regulator 121, the blood transfer rate adjustment unit 160, the linked control display unit 180, and the blood transfer control switching unit 190 have the same as those of the first embodiment, and thus, a description thereof will be omitted.

Similar to the blood removal rate sensor 111, an ultrasonic sensor is used as the blood transfer rate sensor (blood transfer rate measurement means) 112. The blood transfer rate sensor 112 sends a measurement result to the control unit 240.

Needless to say, the blood transfer rate measurement means includes measurement means for measuring a blood transfer rate, and includes measurement means for measuring various blood removal rate parameters for specifying the blood transfer rate.

The blood transfer rate parameters are parameters which change in correspondence with a blood transfer rate, and needless to say, include a blood transfer rate. That is, the blood transfer rate parameters include various parameters for specifying the blood transfer rate, for example, the flow speed of transferred blood in a case where a cross-sectional flow path area of the blood transfer line is already known, and a parameter (for example, a change in ultrasonic wave frequency) for specifying the flow speed.

A comparison between a blood transfer rate parameter and a blood removal rate parameter implies any one of a comparison therebetween in a case where the types of the blood transfer rate parameter and the blood removal rate parameter are the same, a direct comparison therebetween in a case where the types of the blood transfer rate parameter and the blood removal rate parameter are different from each other, and a comparison therebetween after one or both of the blood transfer rate parameter and the blood removal rate parameter are converted into forms in which both can be compared to each other.

The linked blood transfer rate storage unit 170 is formed of an external memory or the like. In the embodiment, the linked blood transfer rate storage unit 170 stores the blood transfer rate (data relating to a linked blood transfer rate) of the centrifugal pump 220 which is measured by the blood transfer rate sensor 112.

The centrifugal pump 220 suctions blood stored in the reservoir 102 via the blood line 103, and transfers the blood to the artificial lung 105 via the first blood transfer line 104 by rotating impeller blades via an AC servo motor or a DC servo motor.

The centrifugal pump 220 is controlled by a control signal output from the control unit 240. The rotational speed of the centrifugal pump 220 in normal control is controlled independently from a blood flow rate. The rotational speed of the centrifugal pump 220 in linked control is controlled such that a blood transfer rate measured by the blood transfer rate sensor 112 is synchronized with a blood removal rate measured by the blood removal rate sensor 111. The rotational speed of the centrifugal pump 220 is feedback controlled in either case.

The blood transfer regulator 122 is provided in the first blood transfer line 104. The blood transfer regulator 122 includes a clamper 122A formed of a pair of clamp members; a servo motor (not shown) that operates the clamper 122A; and a blood transfer regulator operation unit 122B. An operator blocks the first blood transfer line 104 by adjusting the amount of clamp (the amount of pinch) of the clamper 122A via the servo motor driven by manually operating the blood transfer regulator operation unit 122B, and thus, the back flowing of blood when the centrifugal pump 220 stops is prevented.

Figure 8:
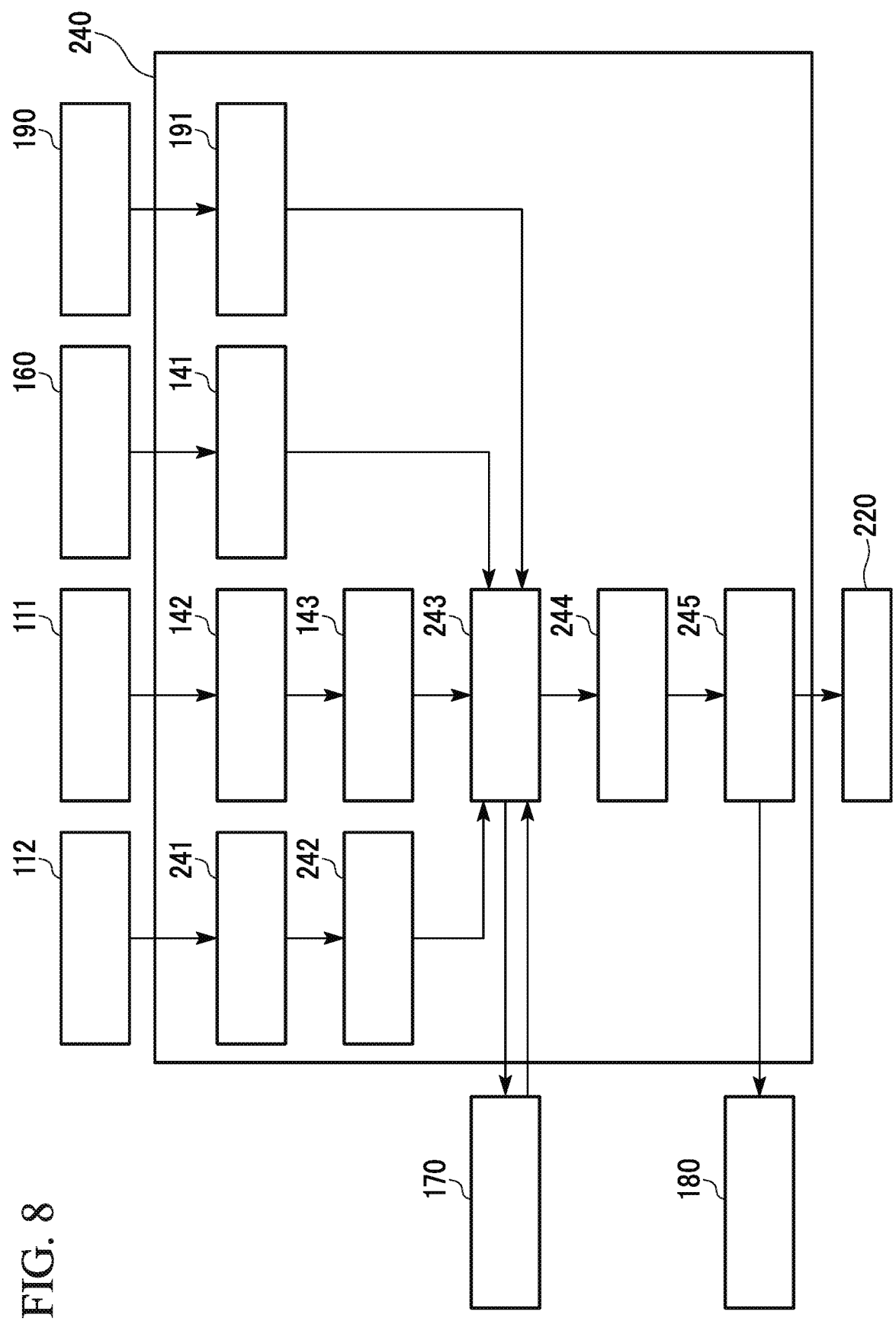
FIG. 8 is a block diagram showing a schematic configuration of a control unit of the artificial heart and lung apparatus of the second embodiment of the present invention.

Hereinafter, a schematic configuration of the control unit 240 will be described with reference to FIG. 8. FIG. 8 is a block diagram showing the schematic configuration of the control unit 240 of the second embodiment.

The control unit 240 includes the blood transfer rate adjustment data receiving unit 141; the blood removal rate signal input receiving unit 142; the blood removal rate calculation unit 143; a blood transfer rate signal receiving unit 241; a blood transfer rate calculation unit 242; a target blood transfer rate calculation unit 243; a centrifugal pump control amount calculation unit 244; a centrifugal pump control unit 245; and the blood transfer control switching instruction receiving unit 191.

The control unit 240 is connected to the blood removal rate sensor 111, the blood transfer rate sensor 112, the blood transfer rate adjustment unit 160, the linked blood transfer rate storage unit 170, the linked control display unit 180, the blood transfer control switching unit 190, and the centrifugal pump 220 via cables.

The blood transfer rate adjustment data receiving unit 141, the blood removal rate signal input receiving unit 142, the blood removal rate calculation unit 143, and the blood transfer control switching instruction receiving unit 191 have the same as those of the first embodiment, and thus, a description thereof will be omitted.

The blood transfer rate signal receiving unit 241 is connected to the blood transfer rate sensor 112, and receives a blood transfer rate signal (blood transfer rate parameter signal) sent from the blood transfer rate sensor 112.

The blood transfer rate calculation unit 242 calculates a blood transfer rate according to the blood transfer rate signal sent from the blood transfer rate signal receiving unit 241. Specifically, the blood transfer rate calculation unit 242 is capable of calculating the blood transfer rate by multiplying the blood transfer speed (flow rate parameter), which is calculated from the blood transfer rate signal, by the flow path area of the first blood transfer line 104.

The target blood transfer rate calculation unit 243 calculates target blood transfer rates of the centrifugal pump 220 in the normal control and the linked control.

The calculation of a target blood transfer rate performed by the target blood transfer rate calculation unit 243 switches between the normal control and the linked control according to linked control transition conditions and a blood transfer control switching instruction signal received from the blood transfer control switching instruction receiving unit 191.

Similar to the first embodiment shown in FIG. 3, in the second embodiment, a blood transfer rate measured by the blood transfer rate sensor 112 shown in FIG. 3 is used in the switching of the artificial heart and lung apparatus 200 between the normal control and the linked control. Other conditions are the same as those of the first embodiment.

The target blood transfer rate calculation unit 243 calculates a target blood transfer rate in the normal control according to the blood transfer rate adjustment data received from the blood transfer rate adjustment data receiving unit 141 and the blood transfer rate read from the blood transfer rate storage unit 170.

The target blood transfer rate calculation unit 243 calculates a target blood transfer rate in the linked control according to the blood transfer rate received from the blood transfer rate calculation unit 242.

In the linked control, the target blood transfer rate calculation unit 243 stores the blood transfer rate, which has been received from the blood transfer rate calculation unit 242, in the linked blood transfer rate storage unit 170.

In the embodiment, in the linked control, the blood transfer rate of the centrifugal pump 220, which flows through the first blood transfer line 104 and the second blood transfer line 106, is set to coincide with a blood removal rate, and the blood transfer rate is synchronized with the blood removal rate.

The synchronization of the blood transfer rate of the centrifugal pump 220 with the blood removal rate is one aspect in which the blood transfer rate is controlled to be in a specific range (for example, in a range represented by a ratio to the blood removal rate, or in a range represented by a difference in flow rate with respect to the blood removal rate) with respect to the blood removal rate.

<Target Blood Transfer Rate (Blood Transfer Rate which is Target) Calculation Process in Normal Control>

Figure 9:
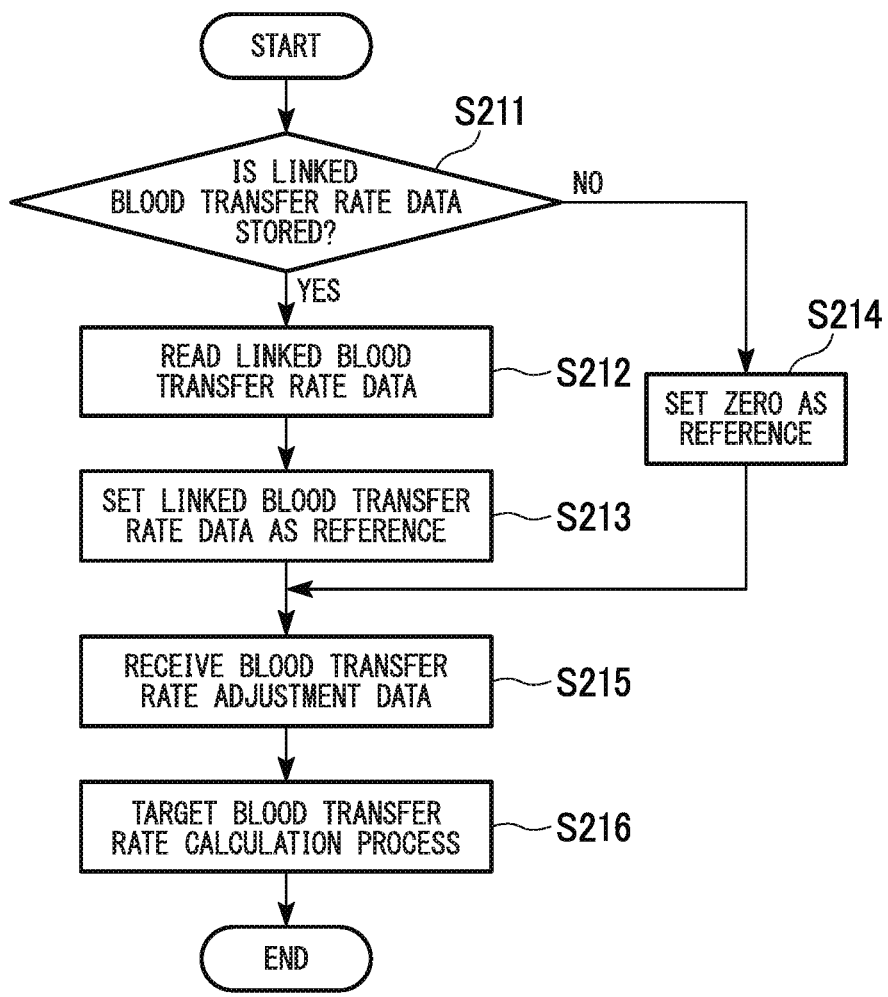
FIG. 9 is a flowchart showing an example of a target blood transfer rate calculation process in the normal control of the artificial heart and lung apparatus of the second embodiment of the present invention.

Hereinafter, a target blood transfer rate calculation process in the normal control of the artificial heart and lung apparatus 200 of the second embodiment will be described with reference to FIG. 9. FIG. 9 is a flowchart showing an example of the target blood transfer rate calculation process in the normal control which is performed by the target blood transfer rate calculation unit 243.

(1) First, the target blood transfer rate calculation unit 243 determines whether the linked blood transfer rate storage unit 170 stores linked blood transfer rate data (S211).

In a case where the linked blood transfer rate data is stored (S211: Yes), the process proceeds to S212. In a case where there is no instruction indicating a transition to the linked control (S211: No), the process proceeds to S214.

(2) Subsequently, the target blood transfer rate calculation unit 243 reads the linked blood transfer rate data from the linked blood transfer rate storage unit 170 (S212).

(3) The target blood transfer rate calculation unit 243 sets the read linked blood transfer rate data as a reference when calculating a blood transfer rate (S213). If S213 is executed, the process proceeds to S215.

(4) The target blood transfer rate calculation unit 243 sets "zero" as a reference when calculating a target blood transfer rate (S214).

(5) Subsequently, the target blood transfer rate calculation unit 243 receives blood transfer rate adjustment data (S215).

(6) Subsequently, the target blood transfer rate calculation unit 243 calculates a target blood transfer rate according to the received blood transfer rate adjustment data (S216).

In the calculation of the blood transfer rate, for example, the blood transfer rate adjustment data is added to (increased or decreased) the reference set in S213 or S214.

While the normal control of the artificial heart and lung apparatus 200 is performed, the process from S211 to S216 is repeatedly executed at predetermined intervals.

The centrifugal pump control amount calculation unit 244 compares the target blood transfer rate, which has been sent from the target blood transfer rate calculation unit 243, to the blood transfer rate, and calculates a rotational speed (control amount) via feedback control.

The control amount of the centrifugal pump 220 in the linked control is a control amount that synchronizes the blood transfer rate with the blood removal rate.

The centrifugal pump control unit 245 outputs a signal to the centrifugal pump 220 in correspondence with the control amount received from the centrifugal pump control amount calculation unit 244.

In a case where blood transfer control transitions to the linked control, the centrifugal pump control unit 245 turns on the linked control display unit 180.

<Normal Control>

Hereinafter, an example of an operational sequence in a case where the normal control of a blood transfer rate is performed by operating the blood transfer rate adjustment unit 160 of the artificial heart and lung apparatus 200 of the second embodiment will be described with reference to FIG. 10.

Figure 10:
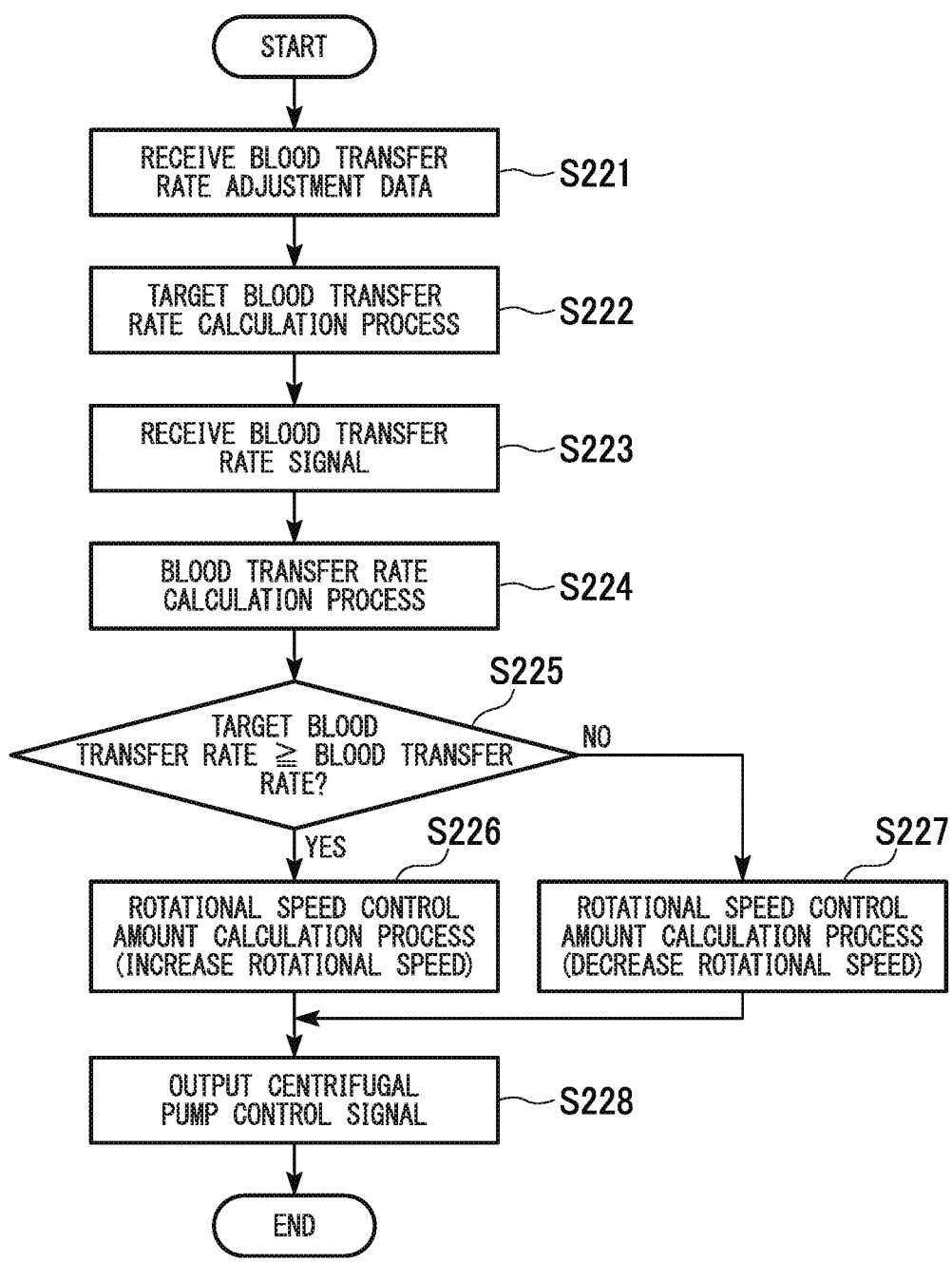
FIG. 10 is a flowchart showing an example of an operational sequence in the normal control of the artificial heart and lung apparatus of the second embodiment of the present invention.

FIG. 10 is a flowchart showing an example of the operational sequence in the normal control of the artificial heart and lung apparatus 200.

(1) First, the blood transfer rate adjustment data receiving unit 141 receives blood transfer rate adjustment data (S221).

(2) Subsequently, the target blood transfer rate calculation unit 243 calculates a target blood transfer rate according to the blood transfer rate adjustment data (S222).

(3) Subsequently, the blood transfer rate signal receiving unit 241 receives a blood transfer rate signal (blood transfer rate parameter signal) (S223).

(4) Subsequently, the blood transfer rate calculation unit 242 calculates a blood transfer rate according to the received blood transfer rate signal (S224).

(5) Subsequently, the target blood transfer rate calculated in S222 is compared to the blood transfer rate calculated in S224, a value of (the target blood transfer rate minus the blood transfer rate) is calculated, and it is determined whether the target blood transfer rate is greater than or equal to the blood transfer rate (S225).

In a case where the target blood transfer rate is greater than or equal to the blood transfer rate (S225: Yes), the centrifugal pump control unit 245 transitions to a step (S226) in which a control amount (increased rotational speed) of the centrifugal pump 220 is calculated. In a case where the target blood transfer rate is less than the blood transfer rate (S225: No), the centrifugal pump control unit 245 transitions to a step (S227) in which a control amount (decreased rotational speed) of the centrifugal pump 220 is calculated.

In a case where the target blood transfer rate is equal to the blood transfer rate, the control amount (increased rotational speed) becomes zero.

(6) Subsequently, the centrifugal pump control unit 245 outputs a signal to the centrifugal pump 220 in correspondence with the control amount calculated in S226 or S227 (S228).

The process from S221 to S228 is repeatedly executed at predetermined intervals until the artificial heart and lung apparatus 200 transitions to the linked control.

<Linked Control>

Figure 11:
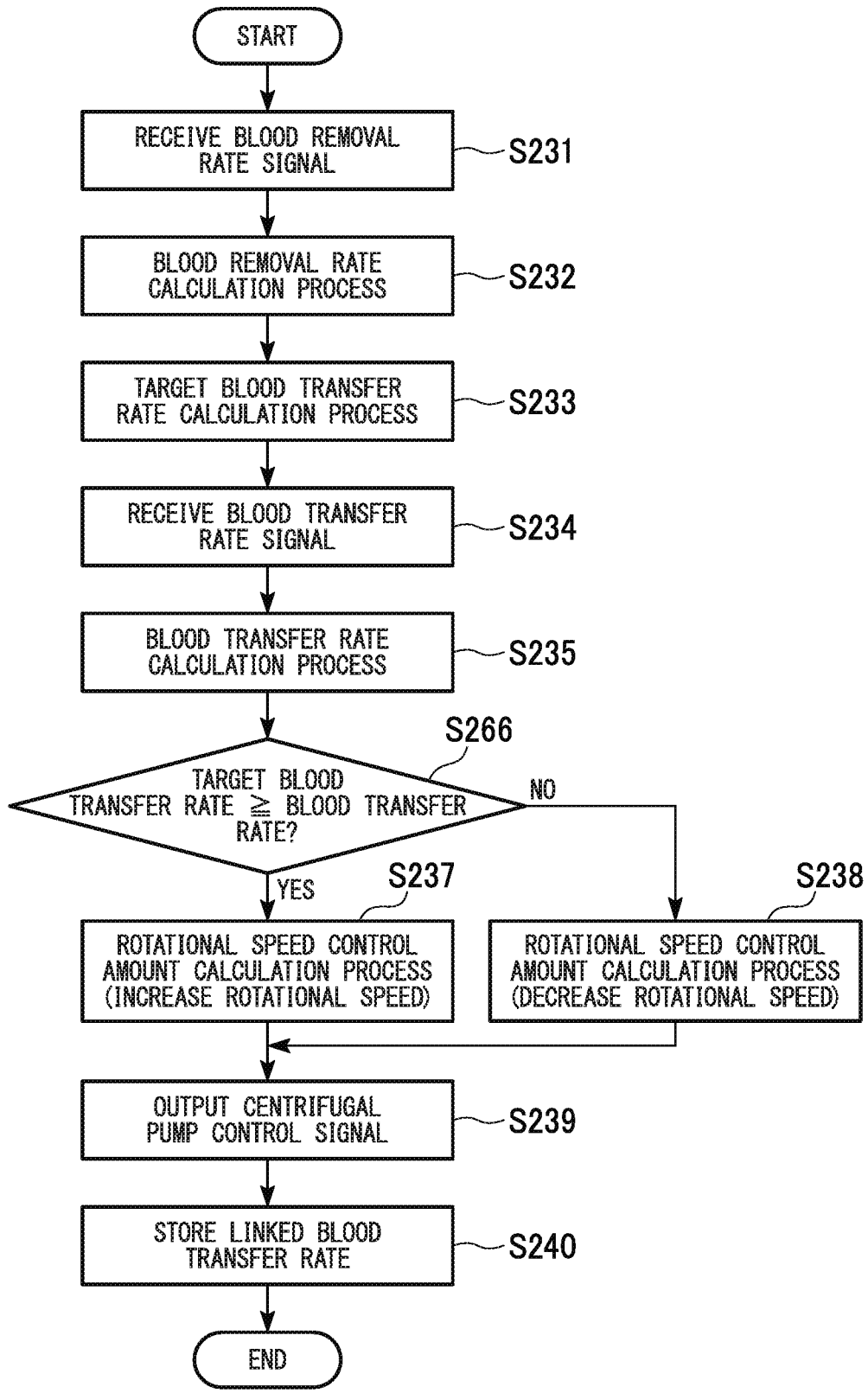
FIG. 11 is a flowchart showing an example of an operational sequence in the linked control of the artificial heart and lung apparatus of the second embodiment of the present invention.
Figure 12:
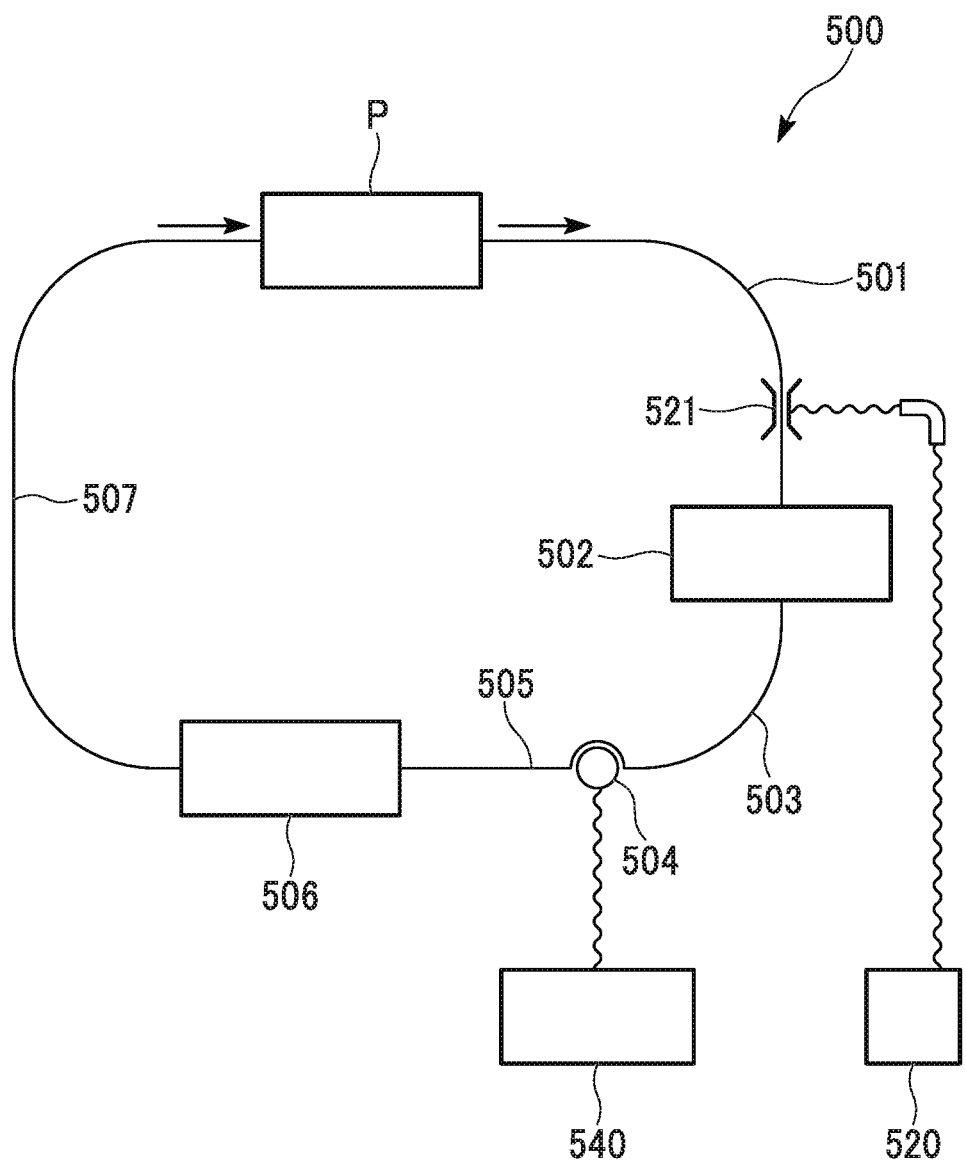
FIG. 12 is a circuit diagram showing a schematic configuration of an artificial heart and lung apparatus in the related art.

Hereinafter, an example of an operational sequence in the linked control of the artificial heart and lung apparatus 200 will be described with reference to FIG. 11. FIG. 11 is a flowchart showing an example of the operational sequence in the linked control of the artificial heart and lung apparatus 200.

(1) First, the blood removal rate signal input receiving unit 142 receives a blood removal rate signal (blood removal rate parameter signal) (S231).

(2) Subsequently, the blood removal rate calculation unit 143 calculates a blood removal rate according to the received blood removal rate signal (S232).

(3) Subsequently, the target blood transfer rate calculation unit 243 calculates a target blood transfer rate according to the blood removal rate calculated in S232 (S233).

(4) Subsequently, the blood transfer rate signal receiving unit 241 receives a blood transfer rate signal (blood transfer rate parameter signal) (S234).

(5) Subsequently, the blood transfer rate calculation unit 242 calculates a blood transfer rate according to the received blood transfer rate signal (S235).

(6) Subsequently, the target blood transfer rate calculated in S233 is compared to the blood transfer rate calculated in S235, a value of (the target blood transfer rate minus the blood transfer rate) is calculated, and it is determined whether the target blood transfer rate is greater than or equal to the blood transfer rate (S236).

In a case where the target blood transfer rate is greater than or equal to the blood transfer rate (S236: Yes), the process proceeds to a step (S237) in which a control amount (increased rotational speed) of the centrifugal pump 220 is calculated. In a case where the target blood transfer rate is less than the blood transfer rate (S236: No), the process proceeds to a step (S238) in which a control amount (decreased rotational speed) of the centrifugal pump 220 is calculated.

In a case where the target blood transfer rate is equal to the blood transfer rate, the control amount (increased rotational speed) becomes zero.

(7) Subsequently, the centrifugal pump control unit 245 outputs a signal to the centrifugal pump 220 in correspondence with the control amount calculated in S237 or S238 (S239).

(8) Subsequently, the target blood transfer rate calculation unit 243 stores a linked blood transfer rate (data relating to a linked blood transfer rate) of the centrifugal pump 220 in the linked blood transfer rate storage unit 170 (S240).

The process from S231 to S240 is repeatedly executed at predetermined intervals until blood transfer control transitions to the normal control or surgery is complete and the linked control ends.

<Switching between Normal Control and Linked Control>

Since switching between the normal control and the linked control is performed in the same manner as that of the artificial heart and lung apparatus 100 of the first embodiment shown in FIG. 6, a description thereof will be omitted.

In the artificial heart and lung apparatus 200 of the second embodiment, the control unit 240 synchronizes the blood transfer rate of the centrifugal pump 220 with the blood removal rate. As a result, even if the blood removal rate changes, it is possible to stably circulate blood.

Since the blood transfer rate adjustment unit 160 includes an encoder with a latch through which an operation amount from an arbitrary position (circumferential position) can be input, the artificial heart and lung apparatus 200 of the second embodiment has a simple structure. Accordingly, in a case where blood transfer control transitions from the linked control to the normal control, it is not necessary to reset the blood transfer rate adjustment unit 160 by manually returning the blood transfer rate adjustment unit 160 to a reference position. As a result, adjustment in the normal control can be efficient due to the elimination of the labor and time required to perform reset.

In the artificial heart and lung apparatus 200 of the second embodiment, in a case where the blood transfer rate of the centrifugal pump 220 in the linked control is significantly smaller than a blood transfer rate that is set by the blood transfer rate adjustment unit in the normal control before the blood transfer control transitions to the linked control, it is possible to prevent blood from being transferred at the previous blood transfer rate, which has been set by the blood transfer rate adjustment unit, after transitioning to the normal control, and it is possible to stably circulate blood.

In a case where the linked control is not continuously performed, and blood transfer control transitions to the normal control, it is possible to adjust the normal control without the stopping of the blood circulation system, and thus, it is possible to efficiently circulate blood.

In the artificial heart and lung apparatus 200 of the second embodiment, the blood transfer rate (data relating to a linked blood transfer rate) of the centrifugal pump 220 when blood transfer control transitions from the linked control to the normal control is stored in the linked blood transfer rate storage unit 170, and it is possible to adjust a blood transfer rate in the normal control with respect to the blood transfer rate stored in the linked blood transfer rate storage unit 170. Accordingly, even if the blood removal rate which is set before the blood transfer control transitions to the linked control significantly changes after transitioning to the linked control, it is possible to stably adjust the blood transfer rate after transitioning to the normal control.

Since the artificial heart and lung apparatus 200 of the second embodiment includes the centrifugal pump 220 as the blood transfer pump, it is possible to promptly transfer blood at a stable blood transfer rate.

In the artificial heart and lung apparatus 200 of the second embodiment, the blood removal regulator 121 is provided in the blood removal line 101, and thus, it is possible to suitably adjust a blood removal rate.

Since the blood transfer regulator 122 is provided in the first blood transfer line 104, the blood transfer regulator 122 is capable of preventing the back flowing of blood by blocking the first blood transfer line 104 when the centrifugal pump 220 stops.

In the artificial heart and lung apparatus 200 of the second embodiment, the centrifugal pump 220 is used as a blood transfer pump, and thus, it is possible to promptly transfer blood at a stable blood transfer rate.

The present invention is not limited to the embodiments, and changes can be made to the embodiments in various forms insofar as the changes do not depart from the concept of the invention.

In the artificial heart and lung apparatuses 100 and 200 of the embodiments, the blood transfer rate is synchronized with the blood removal rate. Alternatively, the blood transfer rate may be adjusted to be in a specific range with respect to the blood removal rate.

In the embodiments, the blood transfer rate adjustment unit 160 includes an encoder and a counter. Alternatively, a counter may be separated from an encoder, and may be disposed as a portion of each of the control units 140 and 240.

Instead of an encoder, a device in which an increase and decrease amount is instructed via a (+) press switch and a (−) press switch may be used as an operation amount input unit that outputs pulse signals.

In the embodiments, the artificial heart and lung apparatuses 100 and 200 do not stop when switching between the normal control and the linked control. Alternatively, the artificial heart and lung apparatuses 100 and 200 may be configured to stop. In a case where the artificial heart and lung apparatuses 100 and 200 stop and then re-start in this configuration, a blood transfer rate may be adjusted with reference to a linked blood transfer rate stored in the linked blood transfer rate storage unit 170.

In the embodiments, each of the artificial heart and lung apparatuses 100 and 200 includes the linked blood transfer rate storage unit 170. Alternatively, setting as to whether the linked blood transfer rate storage unit 170 is included may be arbitrarily performed.

In the embodiments, the linked blood transfer rate storage unit 170 is an external memory connected to each of the control units 140 and 240. Alternatively, the configuration and disposition of the linked blood transfer rate storage unit 170 may be arbitrarily set.

In the first embodiment, the linked blood transfer rate storage unit 170 stores the blood transfer rate (target blood transfer rate) of the roller pump 120 as data relating to a linked blood transfer rate. In the second embodiment, a blood transfer rate measured by the blood transfer rate sensor 112 is stored. Alternatively, data relating to a linked blood transfer rate may be a parameter, for example, a blood removal rate or a control amount of the blood transfer pump, which is capable of definitively setting the blood transfer rate of the blood transfer pump.

In the embodiments, the blood removal rate sensor 111 and the blood transfer rate sensor 112 which measure the flow speed of blood are respectively used as blood removal rate measurement means and blood transfer rate measurement means. Alternatively, a blood removal rate and a blood transfer rate may be measured by measuring a blood removal rate parameter (including a blood removal rate) other than a blood removal speed and a blood transfer rate parameter (including a blood transfer rate) other than a blood transfer speed.

In the embodiments, ultrasonic sensors are used as the blood removal rate sensor 111 and the blood transfer rate sensor 112. Alternatively, various well-known flow rate measurement means using laser, infrared light, or the like may be used instead of an ultrasonic sensor.

In the embodiments, the roller pump 120 and the centrifugal pump 220 are used as blood transfer pumps. Alternatively, other types of blood transfer pumps may be used.

In the first embodiment, flow rate adjustment means is not provided in the blood transfer lines. Alternatively, flow rate sensors (flow rate parameter measurement means) such as ultrasonic sensors may be suitably provided in the first blood transfer line 104 and the second blood transfer line 106.

In the first embodiment, the blood removal regulator 121 is provided as flow rate adjustment means, and in the second embodiment, the blood removal regulator 121 and the blood transfer regulator 122 are provided as flow rate adjustment means. Alternatively, neither the blood removal regulator 121 nor the blood transfer regulator 122 may be provided. In a case where flow rate adjustment means is provided, setting as to whether either or both of the blood removal regulator 121 and the blood transfer regulator 122 are provided may be suitably performed, and portions of a blood removal line and a blood transfer line, in which the blood removal regulator 121 and the blood transfer regulator 122 are provided, may be suitably set.

Flow rate measurement means other than the blood removal regulator 121 and the blood transfer regulator 122 may be provided.

In the first and second embodiments, the blood removal regulator 121 and the blood removal rate sensor 111 are disposed in the blood removal line 101 in the listed sequence. Alternatively, the blood removal rate sensor 111 and the blood removal regulator 121 are disposed in the listed sequence.

In the second embodiment, the blood transfer regulator 122 and the blood transfer rate sensor 112 are disposed in the first blood transfer line 104 in the listed sequence. Alternatively, the blood transfer regulator 122 and the blood transfer rate sensor 112 may be disposed in the second blood transfer line 106 instead of the first blood transfer line 104. The blood transfer rate sensor 112 and the blood transfer regulator 122 may be disposed in the listed sequence.

In the embodiments, examples of the flowcharts showing schematic steps of controlling the artificial heart and lung apparatuses 100 and 200 are described. Alternatively, control may be performed via methods (algorithms) other than the methods shown in the flowcharts.

In the embodiments, each of the artificial heart and lung apparatuses 100 and 200 includes the reservoir 102. Alternatively, an auxiliary circulation apparatus (blood circulation system) without the reservoir 102 may be used to prevent the occurrence of excessive negative pressure by synchronizing the blood transfer rate with the blood removal rate or adjusting the blood transfer rate to be in a specific range with respect to the blood removal rate.

INDUSTRIAL APPLICABILITY

In the blood circulation system of the invention, if the blood transfer rate of the blood transfer pump is linked with the blood removal rate, it is possible to stably transfer blood, and to efficiently circulate blood.

REFERENCE SIGNS LIST

P: PATIENT (HUMAN BODY)
100, 200: ARTIFICIAL HEART AND LUNG APPARATUS (BLOOD CIRCULATION SYSTEM)
101: BLOOD REMOVAL LINE
102: RESERVOIR
104: FIRST BLOOD TRANSFER LINE (BLOOD TRANSFER LINE)
105: ARTIFICIAL LUNG
106: SECOND BLOOD TRANSFER LINE (BLOOD TRANSFER LINE)
111: BLOOD REMOVAL RATE SENSOR (BLOOD REMOVAL RATE MEASUREMENT MEANS)
112: BLOOD TRANSFER RATE SENSOR (BLOOD TRANSFER RATE MEASUREMENT MEANS)
120: ROLLER PUMP (BLOOD TRANSFER PUMP)
121: BLOOD REMOVAL REGULATOR (FLOW RATE ADJUSTMENT MEANS)
122: BLOOD TRANSFER REGULATOR (FLOW RATE ADJUSTMENT MEANS)
140, 240: CONTROL UNIT
160: BLOOD TRANSFER RATE ADJUSTMENT UNIT (BLOOD TRANSFER RATE ADJUSTMENT MEANS)
170: LINKED BLOOD TRANSFER RATE STORAGE UNIT
190: BLOOD TRANSFER CONTROL SWITCHING UNIT
220: CENTRIFUGAL PUMP (BLOOD TRANSFER PUMP)

What is claimed is:

1. A blood circulation system that can be connected to a human body, and is configured to transfer removed blood to the human body via a blood transfer pump, the system comprising:
    the blood transfer pump;
    a blood removal line through which removed blood flows to the blood transfer pump;
    a blood transfer line that is configured to transfer blood, which is sent from the blood transfer pump, to the human body;
    a blood removal rate sensor that is provided in the blood removal line; and
    a control unit that includes a blood removal rate signal input receiving unit connected to the blood removal rate sensor and performs linked control of the blood transfer pump in correspondence with a blood removal rate measured by the blood removal rate sensor such that a blood transfer rate of the blood transfer pump is in a specific range with respect to the blood removal rate,
    wherein, for a target blood transfer rate of the blood transfer pump in normal control, the blood transfer pump transfers blood independently from the blood removal rate,
    wherein the blood transfer rate is provided to the control unit, and a linked blood transfer rate storage stores data relating to a linked blood transfer rate when blood transfer control transitions from the linked control to the normal control,
    wherein an operation amount input unit is provided, to which an operation amount from an arbitrary position can be input by a manual operation, and which outputs a pulse signal according to the input operation amount, and a counter that adds and subtracts pulse signals output from the operation amount input unit, and outputs a resultant as blood transfer rate adjustment data, and the counter performs a counting operation with respect to the linked blood transfer rate when the blood transfer control transitions from the linked control to the normal control, and wherein the control unit calculates the target blood transfer rate of the blood transfer pump by adding the blood transfer rate adjustment data to the data relating to the linked blood transfer rate stored in the linked blood transfer rate storage.

2. The blood circulation system according to claim 1, wherein an encoder with a knob through which an operation amount from an arbitrary position can be input to the control unit, or a switch through which an increase and decrease amount is instructed.

\* \* \* \* \*